US012716891B2

(12) United States Patent
Howard

(10) Patent No.: US 12,716,891 B2
(45) **Date of Patent: *Aug. 25, 2026**

(54) AUTOMATED PATHOGEN AND ANTIBODY RAPID TEST

(71) Applicant: Genesis Intelligence, LLC, Jacksonville, FL (US)

(72) Inventor: Newton Howard, Potomac, MD (US)

(73) Assignee: Gensis Intelligence, LLC, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/683,924

(22) Filed: Mar. 1, 2022

(65) Prior Publication Data

US 2022/0187288 A1 Jun. 16, 2022

Related U.S. Application Data

(63) Continuation of application No. 16/855,709, filed on Apr. 22, 2020.

(60) Provisional application No. 63/001,291, filed on Mar. 28, 2020, provisional application No. 62/994,165, filed on Mar. 24, 2020, provisional application No. 62/993,222, filed on Mar. 23, 2020, provisional application No. 62/991,906, filed on Mar. 19, 2020, provisional application No. 62/988,320, filed on Mar. 11, 2020.

(51) Int. Cl.

| | |
|---|---|
| ***G01N 33/543*** | (2006.01) |
| ***G01N 15/1433*** | (2024.01) |
| ***G01N 21/64*** | (2006.01) |
| ***G01N 33/533*** | (2006.01) |
| ***G01N 33/569*** | (2006.01) |

(52) U.S. Cl.

CPC ... *G01N 33/54333* (2013.01); *G01N 15/1433* (2024.01); *G01N 21/6428* (2013.01); *G01N 33/533* (2013.01); *G01N 33/56983* (2013.01); *G01N 2021/6439* (2013.01)

(58) Field of Classification Search

None

See application file for complete search history.

(56) References Cited

U.S. PATENT DOCUMENTS

| | | | | |
|---|---|---|---|---|
| 6,649,128 | B1 * | 11/2003 | Meyer | G01N 35/028 422/50 |
| 2003/0219713 | A1 * | 11/2003 | Valencia | G01N 35/00069 435/7.1 |
| 2006/0134713 | A1 * | 6/2006 | Rylatt | G01N 33/543 435/7.92 |
| 2007/0187251 | A1 * | 8/2007 | Ward | G01N 27/44704 204/601 |
| 2010/0248258 | A1 * | 9/2010 | Lee | G01N 33/54386 435/7.1 |
| 2010/0261203 | A1 * | 10/2010 | Cicciarelli | G01N 33/6893 435/7.9 |
| 2015/0132776 | A1 * | 5/2015 | Kasdan | B01L 3/50273 435/287.2 |
| 2017/0284922 | A1 * | 10/2017 | Mermod | G01N 15/1056 |
| 2019/0032114 | A1 * | 1/2019 | Trivedi | B01L 3/5027 |
| 2020/0290038 | A1 * | 9/2020 | Falconnet | G01N 33/54393 |

* cited by examiner

*Primary Examiner* — Ann Montgomery

(74) *Attorney, Agent, or Firm* — Neo IP

(57) ABSTRACT

Embodiments may include a rapid test device that provide rapid detection of pathogen infection and techniques for rapid assessment of immunity to the pathogen. In an embodiment, a device may comprise a mechanism configured to hold a cartridge configured to receive a test sample, the cartridge comprising: a first chamber configured to receive the test sample, the first chamber pre-filled with micromagnetic particles, a first reservoir pre-filled with secondary antibodies labeled with a fluorescent compound, a mechanism configured to move the secondary antibodies from the first reservoir to the first chamber, a computer system to control the mechanism configured to move the magnetic device to: mix the micromagnetic particles with the test sample by moving the micromagnetic particles, mix the micromagnetic particles with the secondary antibodies, and move the micromagnetic particles to the detection region, and circuitry configured to detect fluorescence of the fluorescent compound in the detection region.

9 Claims, 18 Drawing Sheets

(a)
210
214
212
202
208
Direct immobilization strategy
(b)
216
204
208
Protein A/G-mediated immobilization strategy
(c)
206
208
Secondary Ab-mediated immobilization strategy
Secondary Ab
Target Ab
Protein A/G
Antigen
Thiol group 302
306
308
Sample Loaded onto Chip
Mixture of protein sought and contaminant
Low-affinity fluorophore
308
309
310
304
Sample is loaded onto etched capillary columns
308
312
Virus attaches to antibodies, fluorophore simultaneously released
314
+/
Chip indicates positive/negative result
300

400

402

406

408

Sample Loaded on Chip

424

Optical Sensing "Box"

426

Results sent to Phone

404

408

410

412

414

416

Sample is loaded onto etched capillary columns

Virus attaches to antibodies, fluorophore simultaneously released

Concentrated sample is eluted for analysis

418

Light source

420

Wavelength analysis

422

Optical Sensing

Optical Sensing "Box"

Results sent to Phone

Sample Loaded on Chip

Mix magnetic particles/antigen with sample

Mix flour-escent compound with sample

Wash with buffer, move to detection

Light source

Wavelength analysis

Optical Sensing 500 502 504 506 508 510 512 514 516 518 520 522 524 526 528 530 532 534 536 538

1102
Power
Supply
1104
LED Display
&
Membrane
Switch
1106
USB
1108
µController
1110
Servo Motor
Drivers
1112
Detection &
Authentication
1114
LED
Driver
1116
LEDs
500nm
1102
1122
Sample
Cartridge
1118
Servo Motor &
Magnet
1120
Multispectral
Photodiode
Chips
1100

AUTOMATED PATHOGEN AND ANTIBODY RAPID TEST

CROSS-REFERENCE TO RELATED APPLICATIONS

This application is a continuation of U.S. patent application Ser. No. 16/855,709, filed Apr. 22, 2020, which claims the benefit of U.S. Provisional Application No. 62/988,320, filed Mar. 11, 2020, U.S. Provisional Application No. 62/991,906, filed Mar. 19, 2020, U.S. Provisional Application No. 62/993,222, filed Mar. 23, 2020, U.S. Provisional Application No. 62/994,165, filed Mar. 24, 2020, and U.S. Provisional Application No. 63/001,291, filed Mar. 28, 2020, the contents of which are incorporated herein in their entirety.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

BACKGROUND

The present invention relates to a rapid test device that provide rapid detection of pathogen infection and techniques for rapid assessment of a person's immunity to the pathogen, for example, using Microscale Affinity Chromatography (MAC), indirect ELISA, and optical molecular sensing technology.

For example, COVID-19, a disease caused by the novel coronavirus (SARS-CoV-2) that was first reported from Wuhan, China, on Dec. 31, 2019, has been declared an international pandemic by the World Health Organization. The virus is spread between people who are in close contact with one another through respiratory droplets produced by coughing or sneezing. The incubation period of COVID-19 is approximately 14 days, making it difficult to contain and contributing to its rapid spread. Current detection techniques rely on RT-PCR, which is a lengthy process, necessitating well-equipped laboratories and skilled personnel to perform the technique. Rapid screening methods are needed to detect the disease at points of entry, transportation hubs, schools, hospitals, and other areas at high risk for communicating the disease in order to limit the spread of the virus. Furthermore, rapid methods of assessing a person's immunity to the virus are becoming increasingly important as people plan for returning to schools and workplaces after the peak of the epidemic. The need to assess the efficacy of vaccines in development has been recognized and is essential in assessing the "herd immunity" to prevent a resurgence of the pandemic.

Accordingly, a need arises for techniques for rapid detection of pathogen infection and techniques for rapid assessment of a person's immunity to the pathogen.

SUMMARY

Embodiments may include a rapid test device that provide rapid detection of pathogen infection and techniques for rapid assessment of a person's immunity to the pathogen, for example, using Microscale Affinity Chromatography (MAC), indirect ELISA, and optical molecular sensing technology.

For example, embodiments may provide pathogen detection using a marked antibody and fluorescence detection for high sensitivity and fast test time. Such test may be on the order of seconds or minutes instead of hours. An embodiments of a test device may be compact and cost effective and may not need to be cleaned or serviced between tests. Embodiments may include sample cartridges that are pre-filled with the necessary compounds and are ready to accept a liquid saliva sample for immediate testing.

In an embodiment, a device for detecting primary antibodies to a pathogen or the pathogen may comprise a mechanism configured to hold a cartridge configured to receive a test sample, the cartridge comprising: a first chamber configured to receive the test sample, the first chamber pre-filled with micromagnetic particles having antigens adapted to bind to antibodies raised against the pathogen immobilized on the micromagnetic particles, a first reservoir pre-filled with secondary antibodies labeled with a fluorescent compound, the secondary antibodies adapted to bind to antigens that have bound to antibodies raised against the pathogen, and a detection region, a mechanism configured to move a magnetic device relative to the cartridge. a mechanism configured to move the secondary antibodies from the first reservoir to the first chamber, a computer system comprising a processor, memory to store program instructions and data and accessible by the processor, and program instructions stored in the memory and executable by the processor to control the mechanism configured to move the magnetic device to: mix the micromagnetic particles with the test sample by moving the micromagnetic particles, so as to facilitate binding of the antigens immobilized on the micromagnetic particles to the antibodies raised against the pathogen, mix the micromagnetic particles with the secondary antibodies from the first reservoir in the first chamber, so as to facilitate binding of the secondary antibodies labeled with the fluorescent compound to the antigens that have bound to antibodies raised against the pathogen, and move the micromagnetic particles to the detection region after the secondary antibodies labeled with the fluorescent compound have bound to the antigens that have bound to antibodies raised against the pathogen, and circuitry configured to detect fluorescence of the fluorescent compound in the detection region.

In embodiments, the mechanism configured move the magnetic device may comprise a servo motor controlled by the processor and rack and pinion gearing to move the magnetic device. The magnetic device may comprise a permanent magnet or a magnetic coil. The circuitry configured to detect fluorescence of the fluorescent compound may comprise at least one excitation light emitting diode arranged to illuminate the detection region so as to excite fluorescence of the fluorescent compound and at least one photodiode arranged to detect the excited fluorescence of the fluorescent compound in the detection region and to output a signal representing the detected fluorescence. The processor may be configured to receive the signal representing the detected fluorescence and the program instructions stored in the memory may further include program instructions configured to determine presence of primary antibodies to the pathogen or the pathogen based on the received signal. The device may further comprise a display configured to display presence of primary antibodies to the pathogen or the pathogen, wherein the display is connected to the processor, and the program instructions stored in the memory may further include program instructions configured to control the display based on the determined presence of primary antibodies to the pathogen or the pathogen. The cartridge may further comprise a second chamber between the first chamber and the detection region and configured to receive contents of the first chamber, and a second reservoir pre-filled with buffer agent. The device may further comprise a mechanism configured to move the buffer agent from the second reservoir to the second chamber. The program instructions stored in the memory may further include program instructions configured to control the mechanism configured move the magnetic device to move the micromagnetic particles from the first chamber to the second chamber after the secondary antibodies labeled with the fluorescent compound have bound to the antigens that have bound to antibodies raised against the pathogen.

In an embodiment, a method for detecting primary antibodies to a pathogen or the pathogen may comprise mixing micromagnetic particles with a test sample by moving the micromagnetic particles, so as to facilitate binding of the antigens immobilized on the micromagnetic particles to the antibodies raised against the pathogen, wherein the mixing is performed in a cartridge configured to receive the test sample, the cartridge comprising: a first chamber configured to receive the test sample, the first chamber pre-filled with micromagnetic particles having antigens adapted to bind to antibodies raised against the pathogen immobilized on the micromagnetic particles, a first reservoir pre-filled with secondary antibodies labeled with a fluorescent compound, the secondary antibodies adapted to bind to antigens that have bound to antibodies raised against the pathogen, and a detection region, mixing the micromagnetic particles with the secondary antibodies from the first reservoir in the first chamber, wherein the secondary antibodies are moved using a mechanism configured to move the secondary antibodies from the first reservoir to the first chamber, so as to facilitate binding of the secondary antibodies labeled with the fluorescent compound to the antigens that have bound to antibodies raised against the pathogen using a mechanism configured to move a magnetic device relative to the cartridge, moving the micromagnetic particles to the detection region after the secondary antibodies labeled with the fluorescent compound have bound to the antigens that have bound to antibodies raised against the pathogen using the mechanism configured to move a magnetic device relative to the cartridge, and detecting fluorescence of the fluorescent compound in the detection region.

In embodiments, the mechanism configured move the magnetic device may comprise a servo motor controlled by a processor and rack and pinion gearing to move the magnetic device. The magnetic device may comprise a permanent magnet or a magnetic coil. The fluorescence of the fluorescent compound may be detected using circuitry comprising: at least one excitation light emitting diode arranged to illuminate the detection region so as to excite fluorescence of the fluorescent compound and at least one photodiode arranged to detect the excited fluorescence of the fluorescent compound in the detection region and to output a signal representing the detected fluorescence. The method may further comprise determining presence of primary antibodies to the pathogen or the pathogen based on the detected fluorescence of the fluorescent compound. The method may further comprise displaying presence of primary antibodies to the pathogen or the pathogen. The cartridge further comprises: a second chamber between the first chamber and the detection region and configured to receive contents of the first chamber, and a second reservoir pre-filled with buffer agent. The method may further comprise moving the buffer agent from the second reservoir to the second chamber. The method may further comprise moving the micromagnetic particles from the first chamber to the second chamber after the secondary antibodies labeled with the fluorescent compound have bound to the antigens that have bound to antibodies raised against the pathogen.

In an embodiment, a device for detecting primary antibodies to a pathogen or the pathogen in a person may comprise a cartridge configured to receive a test sample from the person, the cartridge comprising at least one chamber configured to receive the test sample, first apparatus configured to mix at least one first reagent reactive to presence of the primary antibodies to the pathogen or the pathogen, second apparatus configured to mix at least one second reagent including a fluorescent compound with the test sample reactive to presence of the at least one first reagent having reacted to presence of the primary antibodies to the pathogen or the pathogen, and circuitry configured to determine presence of primary antibodies to the pathogen or the pathogen by detecting reaction of the second reagent by determining fluorescence of the fluorescent compound.

In embodiments, the first apparatus may comprise a plurality of magnetic particles upon which at least one antigen to primary antibodies to the pathogen has been immobilized, wherein the at least one first reagent comprises the at least one antigen to primary antibodies that has been immobilized on the plurality of magnetic particles. The first apparatus may further comprise apparatus configured to mix the plurality of magnetic particles with the test sample so as to cause the primary antibodies to the pathogen to attach to the antigen. The second apparatus may comprise apparatus configured to mix the magnetic particles having the primary antibodies to the pathogen to attached thereto with the at least one second reagent including a fluorescent compound. The at least one second reagent including a fluorescent compound may comprise at least one secondary antibody labeled with a fluorescent compound. The circuitry configured to determine presence of primary antibodies to the pathogen or the pathogen by detecting reaction of the second reagent by determining fluorescence of the fluorescent compound may comprise a fluorometer. The circuitry configured to determine presence of primary antibodies to the pathogen or the pathogen by detecting reaction of the second reagent by determining fluorescence of the fluorescent compound may comprise a light source configured to excite the fluorescent compound with a of light and an optical sensor configured to detect an emitted spectrum of light from the excited fluorescent compound. The device may further comprise display circuitry configured to display an indication of presence or absence of primary antibodies to the pathogen. The test sample may be saliva. The pathogen may be SARS-CoV-2. The antigen may comprise SARS-CoV-2 S1 protein. The secondary antibodies may comprise IgA, IgM, and IgG and each of IgA, IgM, and IgG may be labeled with a fluorescent compound having a different light emission spectrum. The test sample may comprise saliva, the pathogen is SARS-CoV-2, and the antigen comprises SARS-CoV-2 S1 protein.

For example, in an embodiment, a method of detecting primary antibodies to a pathogen in a person may comprise receiving in a testing device a test sample from the person, mixing with the test sample a plurality of magnetic particles upon which at least one antigen to primary antibodies has been immobilized so as to cause the primary antibodies to the pathogen to attach to the antigen, mixing at least one secondary antibody labeled with a fluorescent compound with the test sample mixed with the magnetic particles so as to cause the at least one secondary antibody to attach to the primary antibodies to the pathogen, and determining presence of primary antibodies to the pathogen by detecting secondary antibody attachment by determining fluorescence of the fluorescent compound.

In embodiments, the test sample may be one of saliva, blood, or a sample obtained with a nasopharyngeal swab. The pathogen may be SARS-CoV-2. The antigen may comprise SARS-CoV-2 S1 protein. The fluorescence of the fluorescent compound may be detected using a fluorometer. The fluorescence of the fluorescent compound may be determined by exciting the fluorescent compound with a spectrum of light, and detecting emitted light from the excited fluorescent compound. The secondary antibodies may comprise IgA, IgM, and IgG and each of IgA, IgM, and IgG is labeled with a fluorescent compound having a different light emission spectrum. The test sample may comprise saliva, the pathogen may be SARS-CoV-2, and the antigen may comprise SARS-CoV-2 S1 protein.

In an embodiment, an apparatus for detecting primary antibodies to a pathogen in a person may comprise a cartridge configured to receive a test sample from the person, the cartridge comprising at least one chamber configured to receive the test sample and containing a plurality of magnetic particles upon which at least one antigen to primary antibodies has been immobilized, and configured to mix the plurality of magnetic particles with the test sample so as to cause the primary antibodies to the pathogen to attach to the antigen, apparatus configured to move the magnetic particles to at least one chamber having at least one secondary antibody labeled with a fluorescent compound, and to mix the at least one secondary antibody with the magnetic particles so as to cause the at least one secondary antibody to attach to the primary antibodies to the pathogen, and circuitry configured to determine presence of primary antibodies to the pathogen by detecting secondary antibody attachment by determining fluorescence of the fluorescent compound.

In embodiments, the test sample may be one of saliva, blood, or a sample obtained with a nasopharyngeal swab. The pathogen may be SARS-CoV-2. The antigen may comprise SARS-CoV-2 S1 protein. The circuitry configured to determine the presence of primary antibodies to the pathogen by detecting secondary antibody attachment by determining fluorescence of the fluorescent compound may comprise a fluorometer. The circuitry configured to determine the presence of primary antibodies to the pathogen by detecting secondary antibody attachment by determining fluorescence of the fluorescent compound may comprises a light source configured to excite the fluorescent compound with a spectrum of light, and an optical sensor configured to detect emitted light from the excited fluorescent compound. The secondary antibodies may comprise IgA, IgM, and IgG and each of IgA, IgM, and IgG is labeled with a fluorescent compound having a different light emission spectrum. The test sample may comprise saliva, the pathogen is SARS-CoV-2, and the antigen may comprise SARS-CoV-2 S1 protein.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Figure 1:
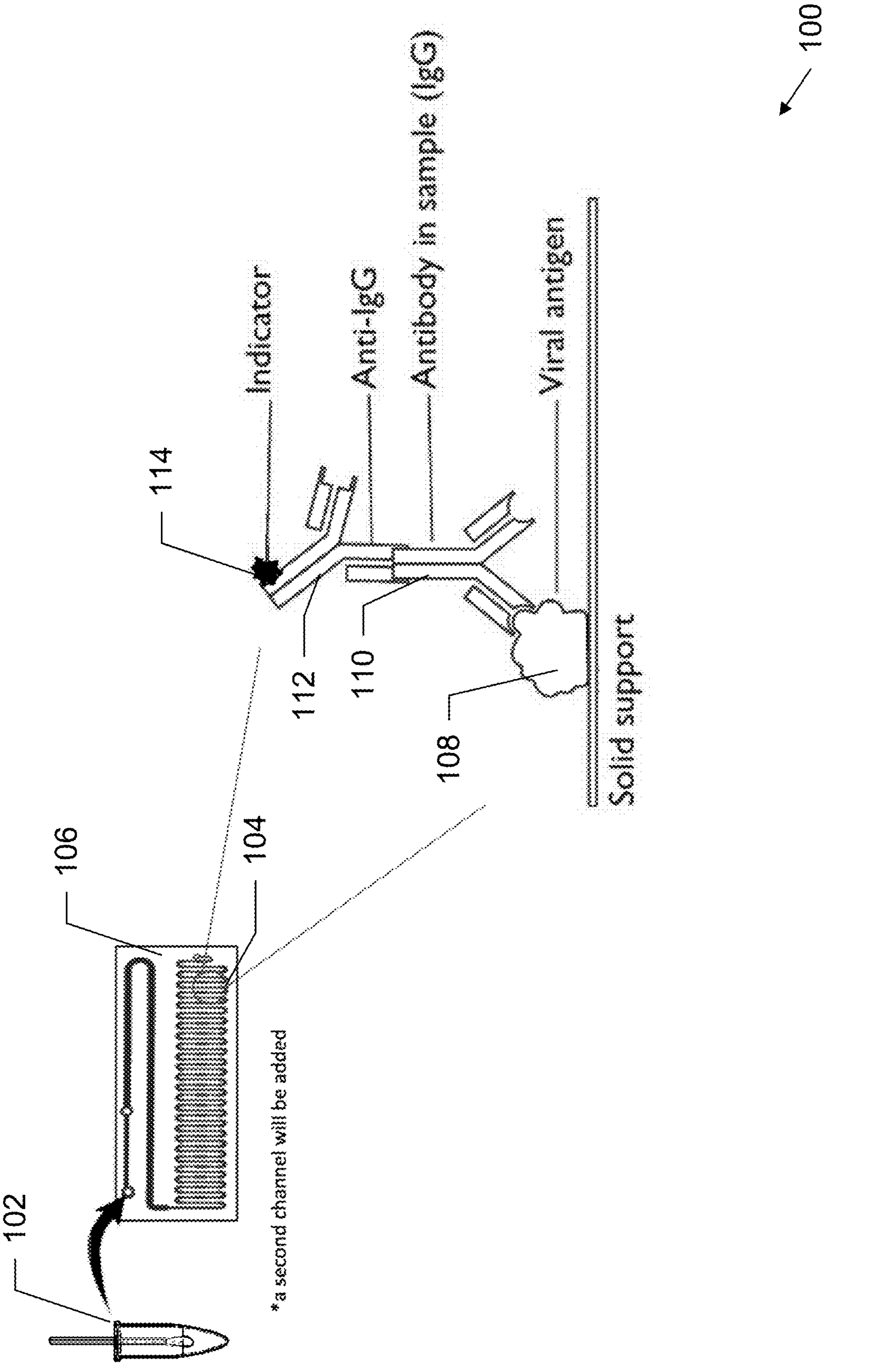
FIG. 1 is an exemplary schematic representation of viral detection. according to embodiments of the present techniques.

Embodiments may include techniques that provide, rapid detection of COVID-19 infection and techniques for rapid assessment of a person's immunity to the virus. For example, embodiments of the present techniques may provide rapid, accurate antibody and viral load testing using Microscale Affinity Chromatography (MAC), indirect ELISA, and optical molecular sensing technology.

Due to the nature of the coronavirus and its ability to spread quickly, there is an immediate need for a portable, instant, non-invasive test that does not require skilled technicians or lab equipment. Currently, only patients who experience severe symptoms are tested in hospitals because tests are too expensive and short in supply. Meanwhile, unscreened patients who have mild or no symptoms continue their daily life, increasing the scale of contamination. The current gold standard for SARS-CoV-2 detection is real time RT-PCR (reverse transcription-polymerase chain reaction). The drawbacks of RT-PCR are multi-faceted in that the equipment is expensive, conducting tests requires expertise, and results take hours to acquire. A complete reaction can be performed in as little as 4 hours, however, the collection of samples, transportation to the lab, preparation of equipment and analysis of results mean significantly longer time is required. Increasing demand for samples to be tested, along with a limited supply of reagents, skilled staff and equipment, can extend the entire RT-PCR process from sample collection to final result to several days. Furthermore, not only is RT-PCR time consuming (average turnaround 3-6 days), but it is also highly labor and cost intensive charging patients and insurance companies up to $4,000 per test. Therefore, there is a recognized need for more rapid, inexpensive tests.

More rapid diagnostic tests have recently come to the market. However, these tests lack reproducibility and have a higher risk of providing false positives. These technologies also utilize forms of sampling that require proximity to the patient, leaving healthcare workers at a higher risk of contracting the disease, such as a nasotracheal swab or a blood sample. The risk to healthcare workers can be minimized by simply acquiring a pooled saliva sample, as SARS-CoV-2 has been detected in saliva of infected patients.

Additionally, evidence shows that convalescent plasma from patients who have recovered from viral infections can be used as a treatment for infection without severe adverse events. The rationale behind convalescent plasma therapy is that the antibodies from a recovered patient's serum might suppress viraemia in an ill patient. The ability to quickly screen recovered patients and administer their convalescent plasma to ill patients is an area lacking in proper diagnostic tests.

After the threat of the pandemic has been mitigated, a need to screen the population to assess the efficacy of vaccines towards the virus to build "herd immunity" has been recognized. Herd immunity (also called community immunity) is an important mechanism by which the larger community is protected. For some diseases, if enough people are immune, transmission of the disease is reduced or eliminated. In the case of protecting against a resurgence of another global pandemic, herd immunity will need to be assessed to determine vulnerable sites with the potential to become hotspots.

Embodiments of the present techniques may include a process to rapidly detect COVID-19 through an alternative method of testing crude saliva samples. Embodiments may utilize lab-on-a-chip technology, where a patient sample containing saliva may be analyzed for antibodies capturing the virus with a simultaneous release of a fluorescent marker ligand. The lab on a chip technology may have the capability to produce a read out in real time using a fluorescent marker passing through a fluorometer. The lab on a chip technology may provide reusable capability, allowing for multiple testing opportunities from one device.

Embodiments may provide a completely self-contained device, with single-use sampling chips, which will reduce the risk of carry-over and minimize error as the sample does not have to be handled after it is loaded. All reagents needed for buffering, dilutions, or washing may be fully contained in a multiple use cartridge, which can be replaced or refilled as needed. Embodiments may be utilized at transportation hubs, such as airports, schools, clinics, and hospitals to limit the spread of the virus, and the technology may be expanded to screen for immunity towards other infectious diseases. In embodiments, the sampling chips and devices may be designed to concurrently detect the presence of both antibodies and virus in the same sample by utilizing the methods described below on the same sampling chip and in the same device.

In embodiments, the testing device may be an automated sandwich immunoassay with fluorescence detection intended for detection of IgA, IgM, IgG antibodies toward SARS-CoV-2 in patients with an active immune response to the virus. Results may identify an immune response to SARS-CoV-2. The screened antibodies are generally detectable in saliva during all phases of infection. Positive results from the embodiments of the testing device are indicative of an active immune response to the virus, that is, that an individual has been infected with SARS-CoV-2 and facilitated a targeted immune response to the virus.

In embodiments, the testing device is intended for use by consumers, clinicians, and point-of-care facilities. In embodiments, the testing device may be used by a variety of consumers in both traditional healthcare settings and elsewhere, for example, in clinics and hospitals, point of entry locations, and private settings, such as at home and in commercial locations. A trained technician is not required to operate the device, and results can easily be read by both licensed healthcare professionals and private individuals. Such access significantly increases the likelihood to determine transmission, resulting on an immediate impact on local and global health.

Embodiments may include a self-contained device that may utilize single-use disposable test cartridges, containing microfluidic chips. Each disposable test cartridge may be self-contained, and the sample may be magnetically moved through the cartridge's microfluidic chip. The test cartridge comes with all necessary reagents, and cleaning supplies are not applicable due to the disposable nature of the cartridges. Additional testing cartridges can be ordered as needed.

Embodiments may include a testing device utilizing automated sandwich immunoassay with fluorescence detection in a microfluidic device for the detection of anti-SARS-CoV-2 IgA, IgM, and/or IgG antibodies in saliva samples. S1 protein from the SARS-CoV-2 virus or a mixture of proteins or their subunits from the virus may be immobilized on, for example, magnetic particles. The magnetic particles may be moved through the use of electromagnets to mix with the saliva sample. In embodiments, magnetic particles that may be used may include, for example, Epoxy Silica Magnetic Particles, 6 μm, Ni-NTA Silica Magnetic Particles, 6 μm, etc.

Embodiments may use the principle of a sandwich immunoassay on magnetic beads. Spike protein specific to the SARS-CoV-2 virus or a subunit of this protein may be immobilized on the surface of silica-coated magnetic beads. Anti-SARS-CoV-2 IgA, IgM, or IgG antibodies from the saliva sample will attach to the antigen immobilized on these beads. Examples of the antigen may include a recombinant SARS-CoV-2 spike protein or the s1 subunit of the spike protein, etc., these proteins may be his-tagged. The magnetic particles will be moved through the cartridge to mix with secondary antibodies labeled with a fluorescent molecule. Examples of fluorescent molecules may include QUANTABLU™ Fluorogenic Substrate, having an excitation maximum at about 325 nm and an emission maximum at about 420 nm, QUANTARED™ Enhanced Chemifluorescent Substrate having an excitation maximum at about 570 nm and an emission maximum at about 585 nm, fluorescein: having an excitation maximum in a range of about 475-495 nm and an emission maximum in a range of about 510-520 nm, etc. The anti-IgA, anti-IgM, and anti-IgG secondary antibodies will serve to detect the binding of antibodies from a positive sample to the immobilized spike protein. Examples of antibodies may include anti-Goat IgG, anti-Goat IgG-FITC labeled, anti-human IgG, anti-human IgM, anti-rabbit IgG, anti-rabbit IgG-FITC labeled, etc. After a wash step with a neutral buffer, to remove excess antibodies, the beads may be moved under a fluorescence detector in the device to detect the signal. Examples of buffers may include tris-buffer, pH ~7 (for wash), phosphate buffer, pH ~7 (for wash), etc. A solution of 10 N HCl may be used for regeneration of the cartridge if desired.

The antibodies raised against SARS-CoV-2 that are present in the saliva from patients with an active immune response to the virus will bind to the immobilized antigen on the particles. The magnetic particles will then be mixed with a fluorescent-labeled secondary antibody, which will bind to anti-virus antibodies, which were present in the sample. In embodiments, the magnetic particles will then be passed into a washing area, then passed under a fluorescent detector, which will detect the signal.

In embodiments, the results may be indicated by a colored light, such as green, yellow or red. Green indicates a positive result, meaning anti-SARS-CoV-2 antibodies have been detected at or above a level that represents current or past infection by SARS-CoV-2 and an active immune response. Yellow indicates an indeterminate result (i.e., user error), and red indicates a negative result, meaning that no anti-SARS-CoV-2 antibodies are present.

In embodiments, testing device capacity may be, for example, several hundred tests per day. In embodiments, the total time required to perform the test may be, for example, five (5) minutes. In embodiments, the number of tests that can be performed per testing device may be one per run.

In embodiments, the estimated shelf life of reagents may be approximately six (6) months with refrigeration. Without refrigeration, shelf life is expected to be shortened, but still likely to be suitable for intermediate to long-term use, for example, approximately three (3) to six (6) months. In embodiments, nM concentrations of antibodies may be used, which are typical concentrations for enzyme based assays. Specific materials to be used may include IgA, IgM, and/or IgG antibodies. Cross-reactivity with other pathogens or antibodies towards other pathogens is not expected. The S1 subunit of the SARS-CoV-2 virus is expected to react specifically with antibodies against the virus.

Detection of Antibody. Embodiments may provide a rapid COVID-19 screen that utilizes a sandwich assay or indirect enzyme-linked immunosorbent assay (ELISA) method. A sandwich immunoassay is a method using two antibodies, which bind to different sites on the antigen or ligand, as shown in FIG. 1. The capture antibody, which is highly specific for the antigen, is attached to a solid surface. The antigen is then added, followed by addition of a second antibody referred to as the detection antibody. The detection antibody binds the antigen at a different epitope than the capture antibody. As a result, the antigen is 'sandwiched' between the two antibodies.

Figure 18:
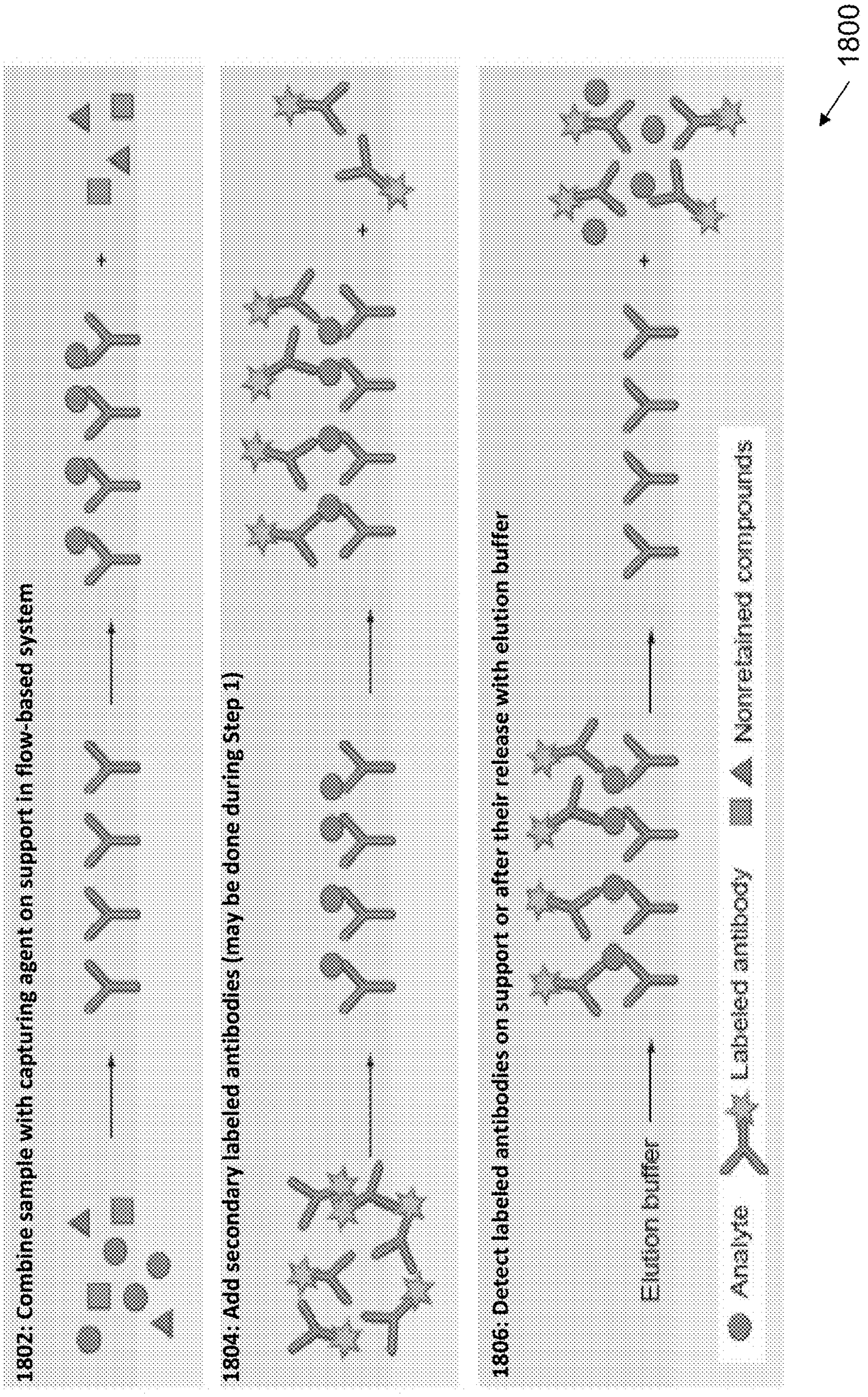
FIG. 18 is an exemplary block diagram of a process of flow-based sandwich immunoassay according to embodiments of the present techniques.

An overview of a flow-based sandwich immunoassay process 1800 according to the present systems and methods is shown in FIG. 18. In process 1800, a Sandwich Immunoassay may be conducted based on two antibodies and binding agents to measure a target compound located in the cartridge of the device. At 1802, a sample may be sample with a first binding agent on a support in a flow-based system. For example, The first binding agent, a COVID-19 (SARS-CoV-2) specific antigen, may be attached to magnetic beads and may be used to capture the anti-COVID-19 IgA, IgM, and IgG antibodies from the saliva sample. At 1804, one or more secondary labeled antibodies may be added (this may instead be done at 1082). Each secondary antibody may contain a fluorescent label that will be used to detect and measure the amount of the capture agent. At 1806, labeled antibodies may be detected, either on the support or after their release with an elution buffer. This approach is highly advantageous as it allows for the detection of any stage of infection (early/late/resolved) by identifying at least three isotypes of antibodies.

As shown in FIG. 1, a crude saliva sample 102 may be injected into a capillary 104 etched onto a silica microfluidic chip 106. For example, saliva may be collected into a 1 mL sterile tube, such as an Eppendorf tube, and transferred with a sterile plastic Pasteur pipette, which will be included with the cartridge. This device is already FDA cleared and widely available. In embodiments, once the cartridge with the saliva sample is put into the device, the remaining steps may be performed automatically by the device. The anti-SARS-CoV-2 antibodies in the sample will be selectively separated by the magnetic beads with spike protein antigen attached. Any particulate matter will be left behind in the initial port where the sample is introduced. In embodiments, there is no sample preparation that needs to be done by the user.

Capillary 104 contains an immobilized SARS-CoV-2 specific antigen 108 to detect SARS-CoV-2 specific antibodies in the sample. If a sample contains antibodies towards the virus, indicating an immune response has occurred, these antibodies 110 will attach to the immobilized antigen. After the sample is run through the capillary, a detection reagent containing a secondary antibody 112 tagged with a fluorescent fluorophore 114 will be introduced. Secondary antibody 112 will recognize blood or saliva-borne antibodies 110 which have attached to immobilized antigen 108. A fluorometer (not shown) will then detect whether secondary antibody binding has occurred. A fluorometer may be used to measure parameters of visible spectrum fluorescence such as its intensity and wavelength distribution of emission spectrum after excitation by a certain spectrum of light. This is described further below with reference to FIG. 4.

This approach is highly advantageous as it allows for the detection of any stage of infection (early, late or resolved) by identifying three isotypes of antibodies.

Immobilization of Antigen. Embodiments may include disposable silica chips 106 be pre-packaged with SARS-CoV-2 specific antigen 108, preferably the S1 protein, directly immobilized onto etched capillaries or onto magnetic particles or beads. Antigen will be diluted in binding solution (0.2 M carbonate-bicarbonate), added to the chip, and incubated. Deactivated surfaces will be used to prevent the need for a blocking step to prevent the non-specific binding of antibodies to the chip. The user need only collect a crude saliva sample, which can then be introduced to the column for detection.

Use of Saliva Sample. Not only is the use of pooled saliva less invasive than blood or nasopharyngeal swabs, but it also minimizes exposure for healthcare workers. Some virus strains have been detected in saliva as long as 29 days after infection. SARS-CoV-2 can present in the saliva in at least three ways. First, SARS-CoV-2 in the lower and upper respiratory tract can enter the oral cavity with the liquid droplets frequently exchanged by these organs. Second, SARS-CoV-2 in the blood can access the mouth via crevicular fluid. Third, major- and minor-salivary gland infection, with subsequent release of SARS-CoV-2 particles in saliva via salivary ducts can cause SARS-CoV-2 to present in the saliva.

Recent tests for other viral diseases, such as HIV, are employing saliva in a similar fashion as they have advantages over blood-based tests in terms of quality, rapidity and convenience. The sensitivity, specificity, positive predictive value and negative predictive value of such HIV tests may be quite high.

Pooled saliva samples can be used to detect both IgG and IgM antibodies, which pass into the mouth through the mucosa, and IgA which are secreted in the mouth. The production of IgM, IgA and IgG antibodies against COVID-19 were found in patient serum as early as day 1 after symptom onset. IgA antibodies were detected in 92.7% of patient samples collected within 0-7 days of symptom onset. IgM and IgA antibodies were both detectable at day 5, and the detection time of IgM, IgA, and IgG against COVID-19 ranged from day 1 to 39 PSO.

One study found the sensitivity and specificity of a lateral flow kit utilizing blood to detect COVID-19 IgM and IgG was 88.66% and 90.63%, respectively (Li, Z., et al., 2020). As the present techniques will additionally test IgA, and since the profile of antibodies in the saliva is similar to that in blood, embodiments of the present techniques should yield similar, if not higher, sensitivity and specificity, as well as a higher accuracy in detecting patients at any stage of infection.

Detection of Antibody. Along with the crude saliva sample, a detection reagent including a secondary antibody labeled with a fluorophore will be introduced to the chip. In embodiments, non-captured sample components and any non-bound secondary antibody can be effectively washed from the device using an application buffer, with the possible use of additives to minimize non-specific binding, as antibodies against the viral antigen are captured by the support. Alternatively, in embodiments, the sample may be applied first to the support, followed by application of the labeled secondary antibodies, with the non-captured or non-bound components again being washed from the support during this process. The conjugated antibodies that are used for this process may be obtained from existing sources or prepared according to well-established procedures for adding fluorescent tags to antibodies or other secondary binding agents. The performance of this device over extended use can be monitored by analyzing positive and negative control samples along with samples.

In addition to detecting immunity, embodiments may be used to verify vaccine immunogenicity. Embodiments may assist researchers in assessing whether the correct antibody profile necessary to protect a patient from reinfection is present. The overall estimated effectiveness of seasonal influenza vaccine for preventing medically attended, laboratory-confirmed influenza virus infection in the 2019 to 2020 flu season was only 45% (Dawood, F. S., et al.). In clinical trials, this method can be used to confirm that antibodies have been raised to the pathogen, meaning the patient has had effective coverage from infection with the pathogen, and has been applied in confirming the effectiveness of the rabies vaccine in dogs and cat (Servat, A., et al., 2007). In addition, immunity to multiple diseases can be screened using a tunable laser and different fluorescent markers.

Figure 3:
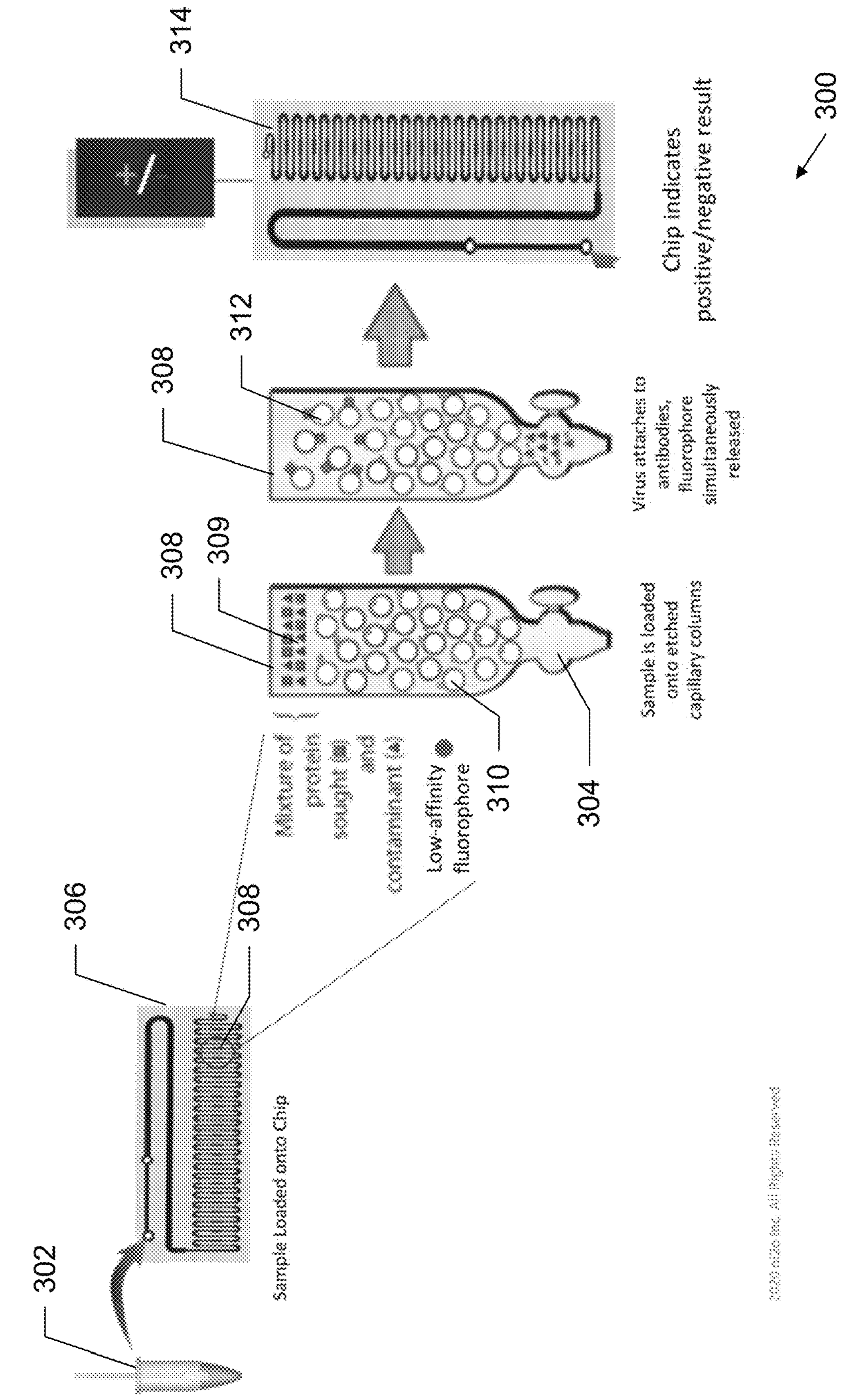
FIG. 3 is an exemplary block diagram of Microscale Affinity Chromatography (MAC) according to embodiments of the present techniques

Rapid COVID-19 Viral Detection. Embodiments may combine viral detection and antibody detection onto one device, or embodiments may provide stand-alone viral or antibody detection product depending on the needs of the market. In embodiments, a rapid COVID-19 viral detection test may employ Microscale Affinity Chromatography (MAC) technology, a separation technique that combines the specificity of antibody recognition and binding with the power, efficiency and speed of modern liquid-phase separations. An example of Microscale Affinity Chromatography 300, according to embodiments of the present techniques, is shown in FIG. 3. A saliva sample 302 is loaded 304 onto a silica microfluidic chamber 306 etched with columns 308 on which primary antibodies 309 towards SARS-CoV-2 are immobilized. Low-affinity fluorophores 310 are weakly bound to these antibodies and are displaced 312 when a sample containing SARS-CoV-2 is introduced. Displaced fluorophores 312 can be considered an indication of a positive result.

In embodiments, antibodies 309 towards SARS-CoV-2 specific proteins will be immobilized on the surface of micro-capillaries 308, microcolumns or etched silica channels on a lab-on-a-chip technology and then tagged with a low affinity competitive ligand 310 containing a fluorophore. A crude patient sample 302, such as saliva, oral or nasopharyngeal swab or blood, can be introduced onto the channel 308 and migrated through the device either by electric charge or a flow system. If SARS-CoV-2 is present in the sample, the virus antigens will be captured on the columns 312 by the antibodies 309 releasing the low affinity ligand 310 to the end of the column. The viral antigens in sample 302 have a higher affinity or liking for the antibodies 309 and therefore will bind to the antibodies 309 and elute the ligand 310 which has a lower affinity. If the low affinity ligands 310 are released from the antibodies 309, a fluorescent marker ligand 310 will be released to indicate a positive sample. If no fluorescence is seen, the sample is negative, because the low affinity ligand 310 was never released from the antibodies.

Sampling. Due to ease of sampling, and lack of necessity for sample preparation, embodiments may use a crude saliva sample 302. The subject will spit into a tube, and a plastic pipette or dropper may be used to transfer the saliva to the etched chip 306. Embodiments may use alternative sampling techniques, such as a nasopharyngeal swab, oral swab or blood sample. In embodiments, a breathalyzer may be interfaced with the COVID-19 detection device. In embodiments, samples from surfaces or air may also be tested using swab methods, or air sampling methods, respectively.

Although the example of Microscale Affinity Chromatography shown in FIG. 3 is described in terms of detection of SARS-CoV-2, the described techniques and apparatus are equally applicable to detection of other pathogens, such as viruses, bacteria, etc.

Figure 2:
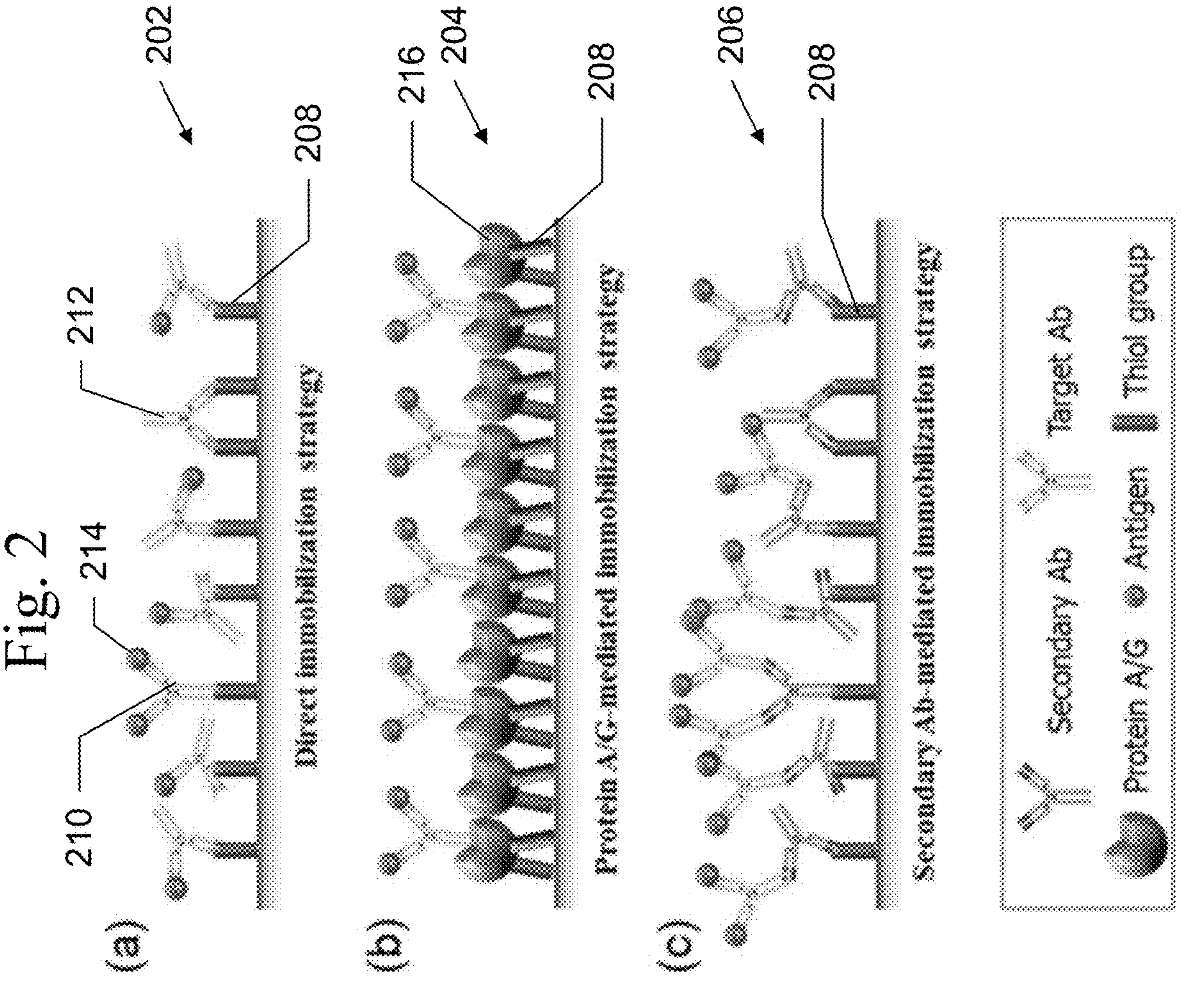
FIG. 2 are exemplary schematic representations of target antibody immobilization on a surface according to embodiments of the present techniques.

Antibody Immobilization to Silica Chip. Exemplary schematic representations of target antibody immobilization on surface, such as gold, using (a) direct target antibody 202, (b) protein A/G-mediated 204, and (c) secondary antibody-mediated immobilization strategies 206 are shown in FIG. 2. In embodiments, antibodies can be attached directly 202 to the walls of a capillary column or microchip channel, however, the orientation of the stationary antibody is key to the binding activity. Antibodies can be immobilized covalently, using a thiol group 208, to a surface or connected to a solid support, although the oriented immobilization of antibodies is considered to be optimal for their effectiveness. An antibody is considered to be properly oriented and perfectly active 210 when the fragment crystallizable region (Fc), which has no antigen binding affinity, is immobilized on a surface, rather than the antigen-binding sites 214 being immobilized on the surface 212. This situation can be produced by a covalent immobilization method, such as carbohydrate groups in an antibody's Fc region. Directly immobilized antibodies do not allow for specific orientation of the antibody, thus, embodiments may use other methods to immobilize antibodies to a silica microfluidic chip, as described below.

It is also possible to achieve proper immobilization through secondary molecule protein A/G-mediated immobilization 204, or secondary Ab-mediated immobilization 206. In protein A/G-mediated immobilization 204, the biomolecules used for antibody immobilization are proteins A and G 216. Protein A is the most successful surface protein able to bind with animal immunoglobulin G (IgGs), but is not effective in certain animal IgGs, such as goat, sheep, cow, and horse. Protein G reacts more with IgGs than protein A and reacts less with other antibody types. A recombinant protein A/G that combines four immunoglobulin-binding domains from protein A and two from protein G can be employed to modify silane-functionalized silicon nitride surfaces.

In Ab-mediated immobilization 206, secondary antibodies 218 are attached to the support and used to recognize the Fc region of the primary antibodies against the target. In this situation, the binding ability of the secondary antibodies should match with the class or subclass of the primary antibody that is to be used immobilized. For example, if the primary antibody is one of mouse IgG subclasses or rabbit IgG, an anti-mouse IgG or anti-rabbit IgG could be used as secondary antibodies. After immobilizing the thiolated-secondary antibody on a silica surface, the target antibody can be captured by the secondary antibody in the correct orientation by binding between the Fab region of the secondary antibody and the Fc region of target antibody.

The example of target antibody immobilization on surface shown in FIG. 2 is not described in terms of detection of any particular pathogen. Rather, the described techniques and apparatus are applicable to detection of many pathogens, such as viruses, such as SARS-CoV-2, bacteria, etc.

Primary Antibody. There are 4 conserved structural proteins across CoVs: the spike (S) protein, membrane (M) protein, envelope (E) protein, and nucleocapsid (N) protein. The S protein is responsible for binding to host cell receptors and viral entry to host cells. The M, E, and N proteins are part of the nucleocapsid of viral particles. S and N genes are under episodic selection as the virus is transmitted between humans. Mutations and adaptation in the S and N genes may affect virus stability and pathogenicity.

Embodiments may use a single primary antibody towards a conserved portion of any of the aforementioned proteins can be used, or embodiments may use a mixture of primary antibodies, which are specific to different mutations of the virus. Monoclonal antibodies towards a conserved portion of the S1 spike surface proteins of SARS-CoV-2 may be a primary target of embodiments. However S2, M, E, or N antibodies may be tested in embodiments.

Figure 4:
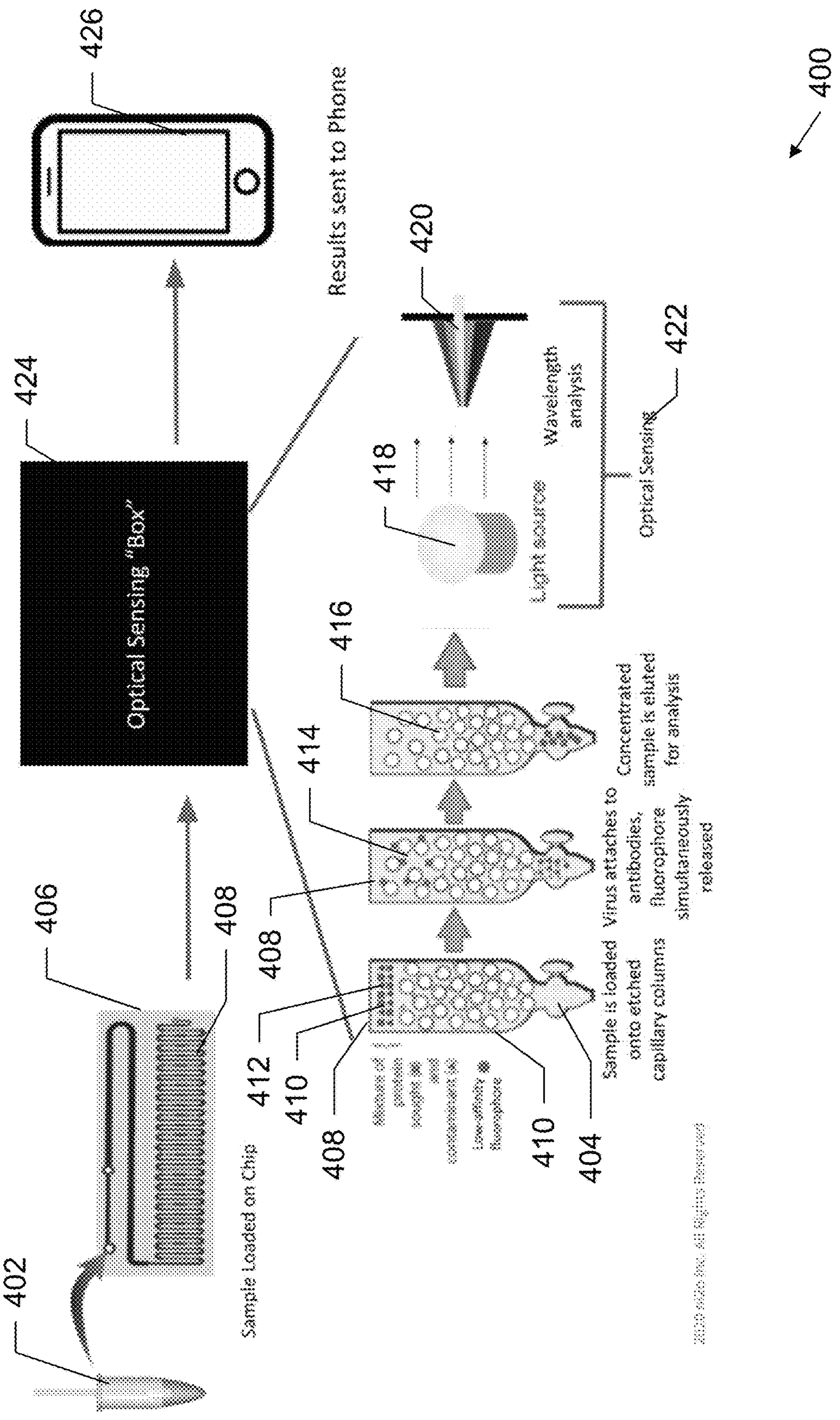
FIG. 4 is an exemplary schematic representation of optical detection according to embodiments of the present techniques.

An example of Microscale Affinity Chromatography with Competitive Affinity Ligand and optical sensing 400, according to embodiments of the present techniques, is shown in FIG. 4. A saliva sample 402 is loaded 404 onto a silica microfluidic chamber 406 etched with columns 408 on which primary antibodies 410 towards SARS-CoV-2 are immobilized. In embodiments, a low-to-moderate affinity, competitive ligand fluorophore 412 will be attached to the primary antibody 410 before the sample 402 is run through the column 408. This fluorescent compound will attach to the primary antibody immobilized on the chip, as visualized in FIG. 2. As the sample 402 is run 414 through the column 408, SARS-CoV-2 within the sample will compete for binding to the primary antibody 410 and, because it has a higher affinity towards the antibody 410, will displace the fluorophore 412. The displaced fluorophore 412 will then be used as an indication of a positive result, and lack thereof can be regarded as a negative result. The concentrated sample may then be eluted 416 for analysis.

In embodiments, fluorescein, a xanthene dye that is highly fluorescent, and detectable even when present in minute quantities may be used. Embodiments may use one of numerous fluorescent markers that are available to serve this function. For example, fluorescein has an excitation maximum in a range of about 475-495 nm and emission in a range of about 510-520 nm, QUANTABLU™ Fluorogenic Substrate, has an excitation maximum at about 325 nm and an emission maximum at about 420 nm, QUANTARED™ Enhanced Chemifluorescent Substrate having an excitation maximum at about 570 nm and an emission maximum at about 585 nm, etc.

Rapid Optical Detection and Improved Sensing. In embodiments, after the concentrated sample containing the biomolecules of interest is eluted 416, additional analysis may be performed using a novel lab-on-chip utilizing wavelength backscattering with at least two wavelengths of light. For example, a light source 418 capable of emitting at least two wavelengths of light, such as a plurality of light emitting diodes, laser diodes, or other lasers, or a tunable laser, may be used to illuminate the eluted sample, exciting the fluorophore 412 and causing light emission 420. The emission spectrum of the light emitted 420 from the fluorophore 412 may be optically sensed 420 and analyzed by, for example, an optical sensing "box" or circuit 422. Optical sensing circuit 422 may perform wavelength and amplitude analysis on the emitted light 420 and may determine the absence, presence, and/or quantity of SARS-CoV-2, or other pathogen, or antibody in the sample 402. In embodiments, such determination may be made in optical sensing circuit 422 and communicated to a computing device 426, such as a smartphone, tablet computer, laptop computer, personal computer, workstation computer, cloud computing service, etc. In embodiments, optical sensing circuit 422 generate data representing the performed wavelength and amplitude analysis and may transmit that data to a computing device 426, such as a smartphone, tablet computer, laptop computer, personal computer, workstation computer, cloud computing service, etc., for determination of the absence, presence, and/or quantity of SARS-CoV-2, or other pathogen, or antibody in the sample 402.

Figure 5:
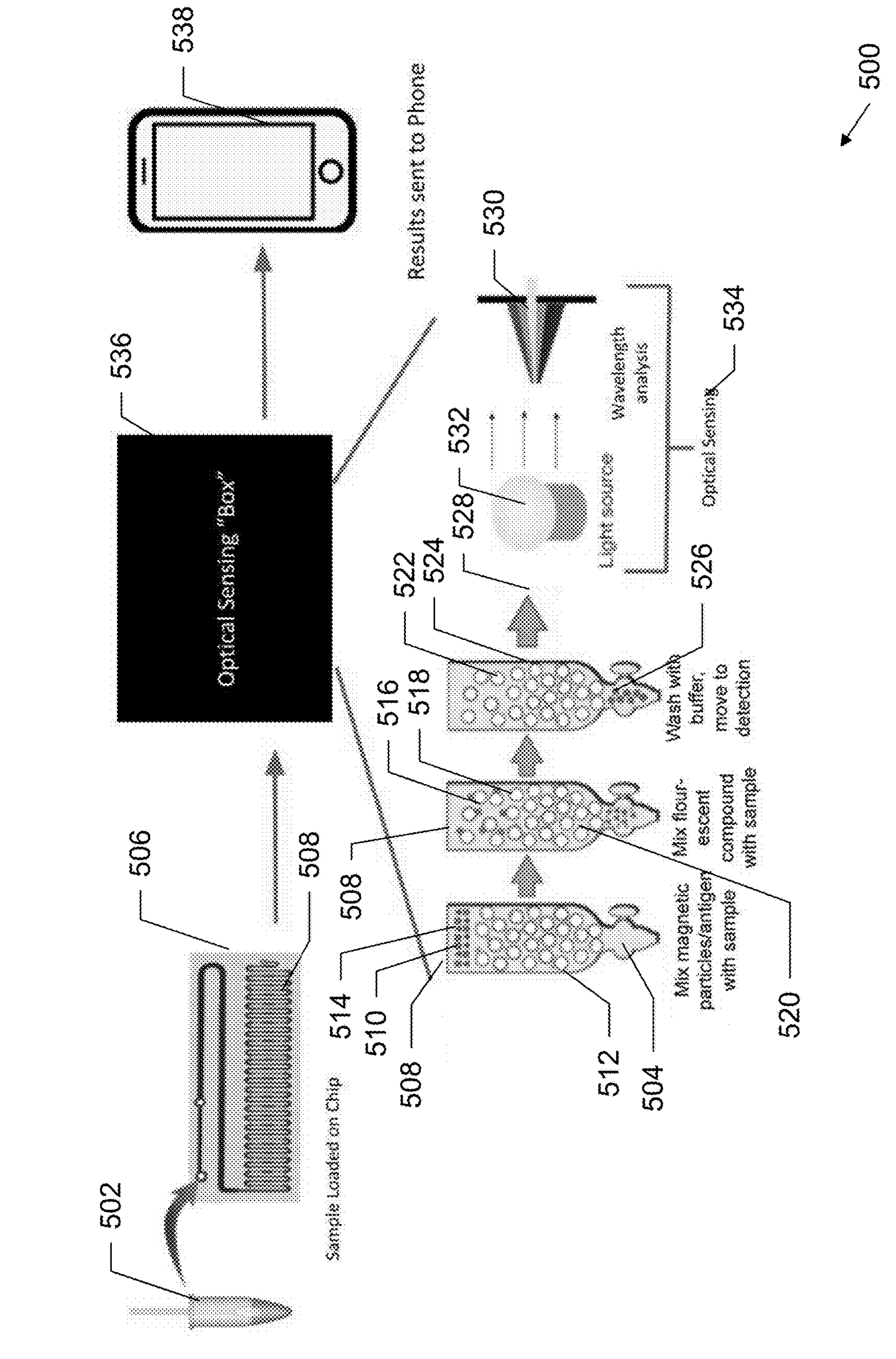
FIG. 5 is an exemplary schematic representation of optical detection according to embodiments of the present techniques.

An example of an embodiment of detection of antibodies raised against SARS-CoV-2 with optical sensing 500, according to embodiments of the present techniques, is shown in FIG. 5. It is best viewed in conjunction with FIG. 6, which is a flow diagram of an embodiment of the testing process 600. Process 600 begins with 602, in which a saliva sample 502 may be collected. The specimen volume may, for example, be less than 1 mL. For example, saliva may be collected into a 1 mL sterile tube, such as an Eppendorf tube, and transferred with a sterile plastic Pasteur pipette. In embodiments, once the cartridge with the saliva sample is put into the device, the remaining steps may be performed automatically by the device.

At 604, particulate matter may be removed from the sample 502 during sample preparation. In embodiments, the anti-SARS-CoV-2 antibodies in the sample will be selectively separated by the magnetic beads with spike protein antigen attached. Any particulate matter will be left behind in the initial port where the sample is introduced. In embodiments, there is no sample preparation that needs to be done by the user. At 606, a portion of saliva sample 502 may be introduced 504 into the cartridge loaded 506 including at least one silica microfluidic chamber 508. For example, about 20-100 μL of the sample 502 may be introduced 504 into the cartridge 506. In embodiments, only a crude approximation of the sample and insertion of the sample by a sterile disposable pipette is necessary. The device may only accept a controlled amount of sample (~30 μL), so the amount of sample measured by the user and inserted into the device need to be exact. The pipette may collect at least 100 μL, which is more than needed. The excess saliva may be discarded with the pipette.

At 608, cartridge 506 may be inserted into the device, and magnetic particles 510 in the cartridge may be moved to the sample in chamber 508 and mixed 512 with the sample. Magnetic particles 510 may have one or more antigens 514 to antibodies raised against SARS-CoV-2 immobilized on the particles. Antibodies present in the sample will bind to the antigens 514 immobilized onto magnetic particles 510. Magnetic particles 510 may be moved by application of electric current by testing device circuitry to magnetic coils. In embodiments, the magnetic coils may be formed on cartridge 506. In embodiments, the magnetic coils may be present in the test device and may be adjacent to or in the vicinity of cartridge 506.

At 610, secondary antibodies (such as IgA, IgM, and IgG) 516 labeled with a fluorescent compound 518, such as fluorescein, QUANTABLU™, QUANTARED™, etc., will also be combined 520 with the magnetic particles and mixed to detect captured antibodies from the sample. At 612, the magnetic particles 510 with attached IgA, IgM, and IgG 516 and fluorescent compound 518, together indicates as 522, may be moved to a washing station 524, and washed 526 using a neutral buffer. At 614, the magnetic particles, etc. 522 may be moved to a detection region 528 to obtain the signal 530 from the fluorescent compound 518 labelling the secondary antibodies 516 on the magnetic particles 510. Antibody isotypes may be distinguished using the color or light emission spectrum of fluorescent compound attached to the secondary antibody.

In embodiments, fluorescein, a xanthene dye that is highly fluorescent, and detectable even when present in minute quantities may be used. Embodiments may use one of numerous fluorescent markers that are available to serve this function. For example, fluorescein has an excitation maximum in a range of about 475-495 nm and emission in a range of about 510-520 nm, QUANTABLU™ Fluorogenic Substrate, has an excitation maximum at about 325 nm and an emission maximum at about 420 nm, QUANTARED™ Enhanced Chemifluorescent Substrate having an excitation maximum at about 570 nm and an emission maximum at about 585 nm, etc.

In embodiments, analysis may be performed using a novel lab-on-chip utilizing wavelength backscattering with at least two wavelengths of light. For example, a light source 532 capable of emitting at least two wavelengths of light, such as a plurality of light emitting diodes, laser diodes, or other lasers, or a tunable laser, may be used to illuminate the washed sample 522, exciting the fluorophore 518 and causing light emission 530. The emission spectrum of the light emitted 530 from the fluorophore 518 may be optically sensed 534 and analyzed by, for example, an optical sensing "box" or circuit 536. Optical sensing circuit 536 may perform wavelength and amplitude analysis on the emitted light 530 and may determine the absence, presence, and/or quantity and isotype of antibody in the sample 522. In embodiments, such determination may be made in optical sensing circuit 536 and communicated to a computing device 538, such as a smartphone, tablet computer, laptop computer, personal computer, workstation computer, cloud computing service, etc. In embodiments, optical sensing circuit 536 may generate data representing the performed wavelength and amplitude analysis and may transmit that data to a computing device 538, such as a smartphone, tablet computer, laptop computer, personal computer, workstation computer, cloud computing service, etc., for determination of the absence, presence, and/or quantity of antibody in the sample 522.

In embodiments, no interpretation of results is needed by the user. The response may be given by a green, yellow, or red indicator per antibody isotype. Green may indicate a positive result, meaning the antibody has been detected against SARS-CoV-2, representing current or past infection by SARS-CoV-2 and an active immune response. An indeterminate or inconclusive result may be shown with a yellow indicator, which is likely due to user error or device malfunction. Red may indicate a negative result, meaning no immune response to SARS-CoV-2 was detected.

In embodiments, the testing device may be a self-contained device that does not require a laboratory for interpretation of results. In embodiments, the positive and negative controls may either be included with the device for consumer use or may be directly built into the self-contained device. For example, a separate channel with magnetic particles labeled with a fluorescent molecule can act as an internal control, which will be directly built into the disposable testing cartridge.

Because each testing cartridge is a single use device, representative cartridges from a given batch may be tested with positive or negative controls and if these are found to be valid and acceptable, other cartridges in the batch may be used. This process can be performed periodically to confirm the validity of the devices in the same batch. The testing device itself may be tested using special-purpose cartridges. Different types of cartridges may have different authentication chips embedded in them, allowing the device to work in "live" or "testing" mode as required. Such authentication chips may include authentication circuitry, identification circuitry, data storage circuitry, etc., and may identify the type of chip, the type of testing being performed, the patient being tested, etc.

An example of a test cartridge 700 is shown in FIGS. **7*a* and 7*b*. An exemplary top view of sample test cartridge 700 is shown in FIG. 7*a*. In this example, test cartridge 700 may include inlet port 702, mixer chamber 704, wash chamber 706, optional amplification chamber 708, mixer reservoir 712, wash reservoir 714, and optional amplification reservoir 716. Reservoirs 712, 714, and 716 may contain solvents, reagents, buffers, etc., in hermitically sealed blisters for storage. Mixer reservoir 712 may be pre-filled with the necessary reagent solvent and micromagnetic beads or particles having antigens to antibodies raised against SARS-CoV-2 immobilized on the particles. Wash reservoir 1004 1005 may be pre-filled with buffer agent. Optional amplification reservoir 716 may be prefilled with enzymatic amplification agents or buffer. Test cartridge 700 may also include a plurality of passages, such as passage 718 between inlet port 702 and chamber 704, passage 720 between chamber 704 and chamber 706, and passage 722 between chamber 706 and chamber 708**.

Figure 6:
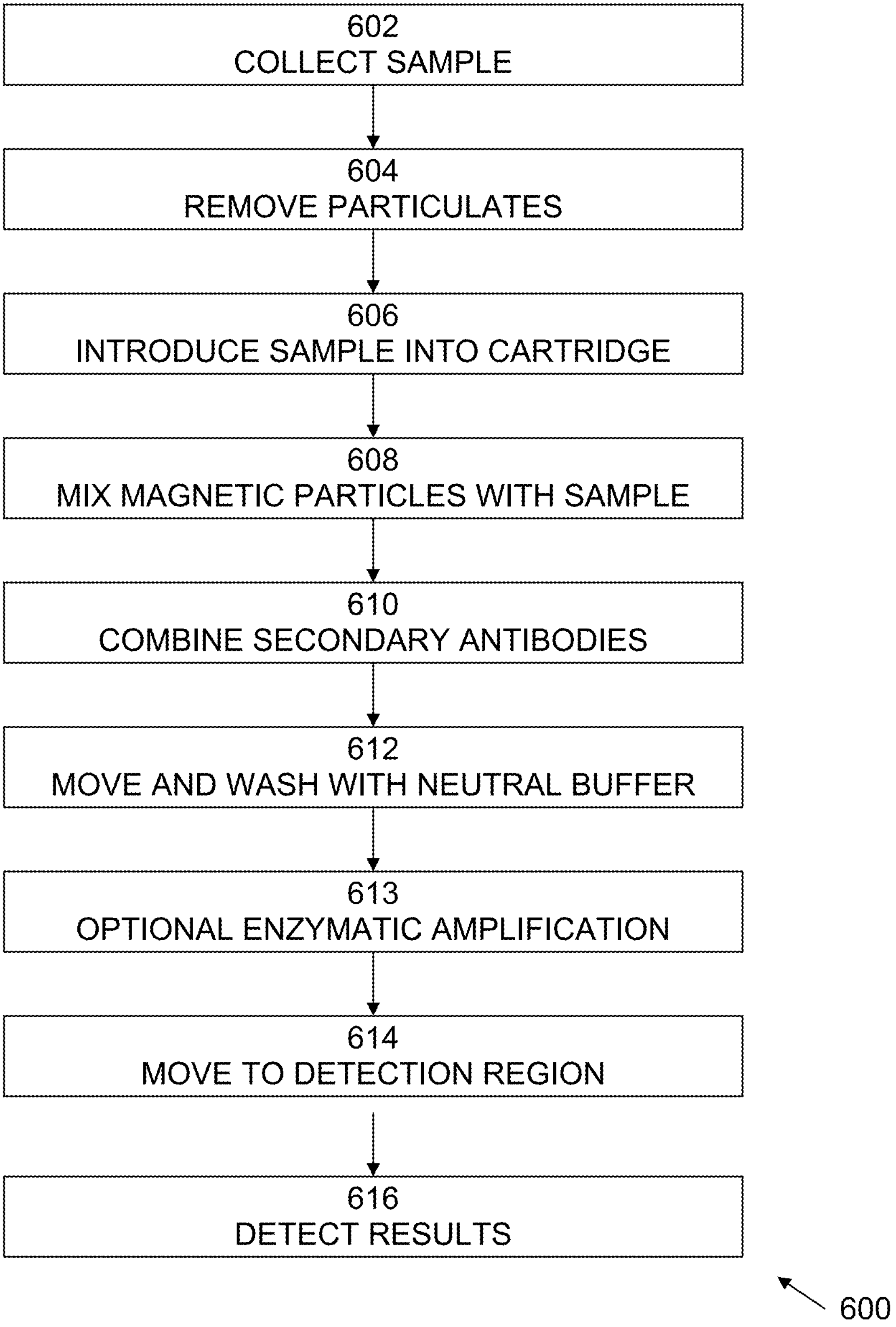
FIG. 6 is an exemplary flow diagram of a testing process according to embodiments of the present techniques

In operation, the testing device may process test cartridge 702, for example, as described in conjunction with FIG. 6. Process 600 begins with 602, in which a saliva sample may be collected. At 606, a portion of saliva sample may be introduced into via inlet port 702 into chamber 704. At 608, cartridge 700 may be inserted into the device, and magnetic particles or beads in chamber 704 may be mixed with the sample. The magnetic particles may have one or more antigens to antibodies raised against SARS-CoV-2 immobilized on the particles. Antibodies present in the sample will bind to the antigens immobilized onto magnetic particles. Mixing may be facilitated by movement of the magnetic particles. The magnetic particles may be moved by application of electric current by testing device circuitry to magnetic coils or by movement of a magnetic field produced by magnetic coils or by a permanent magnet relative to cartridge 700, as described below.

At 610, a reagent solvent in chamber 712, including secondary antibodies (such as IgA, IgM, and IgG) labeled with a fluorescent compound, such as fluorescein, QUANTABLU™, QUANTARED™, etc., may be combined with the magnetic particles and mixed in chamber 704 to detect captured antibodies from the sample. At 612, the magnetic particles with attached IgA, IgM, and IgG and fluorescent compound may be moved to a washing station in chamber 706, and washed using a neutral buffer from chamber 714. At 613, the magnetic particles may optionally be moved into optional enzymatic amplification chamber 708 and optionally mixed with enzymatic amplification agents or buffer from optional amplification reservoir 716. At 614, the magnetic particles may be moved to a detection region in chamber 710 to obtain the signal from the fluorescent compound labelling the secondary antibodies 516 on the magnetic particles. Antibody isotypes may be distinguished using the color or light emission spectrum of fluorescent compound attached to the secondary antibody.

Figure 7B:
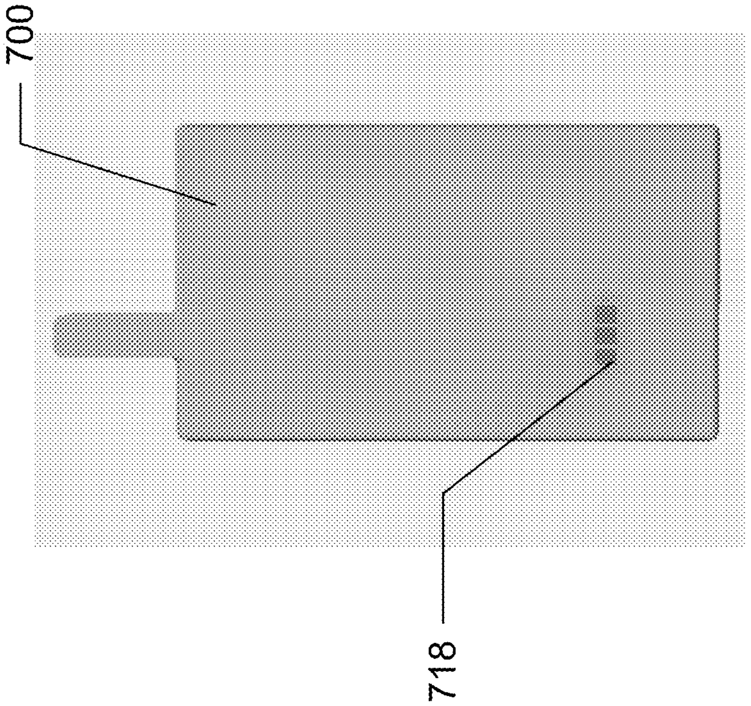
FIG. 7*b* is an exemplary bottom view of sample test cartridge according to embodiments of the present techniques.
Figure 7A:
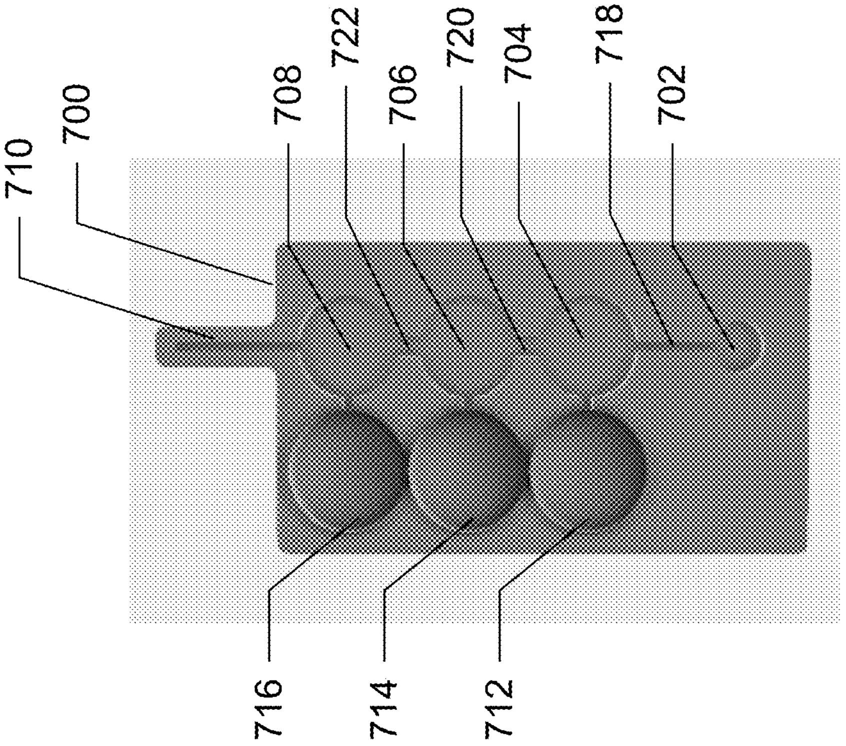
FIG. 7*a* is an exemplary top view of sample test cartridge according to embodiments of the present techniques.

An exemplary bottom view of test cartridge 700 is shown in FIG. 7*b*. In this example, test cartridge 700 may include Authentication Chip 718.

Figure 8:
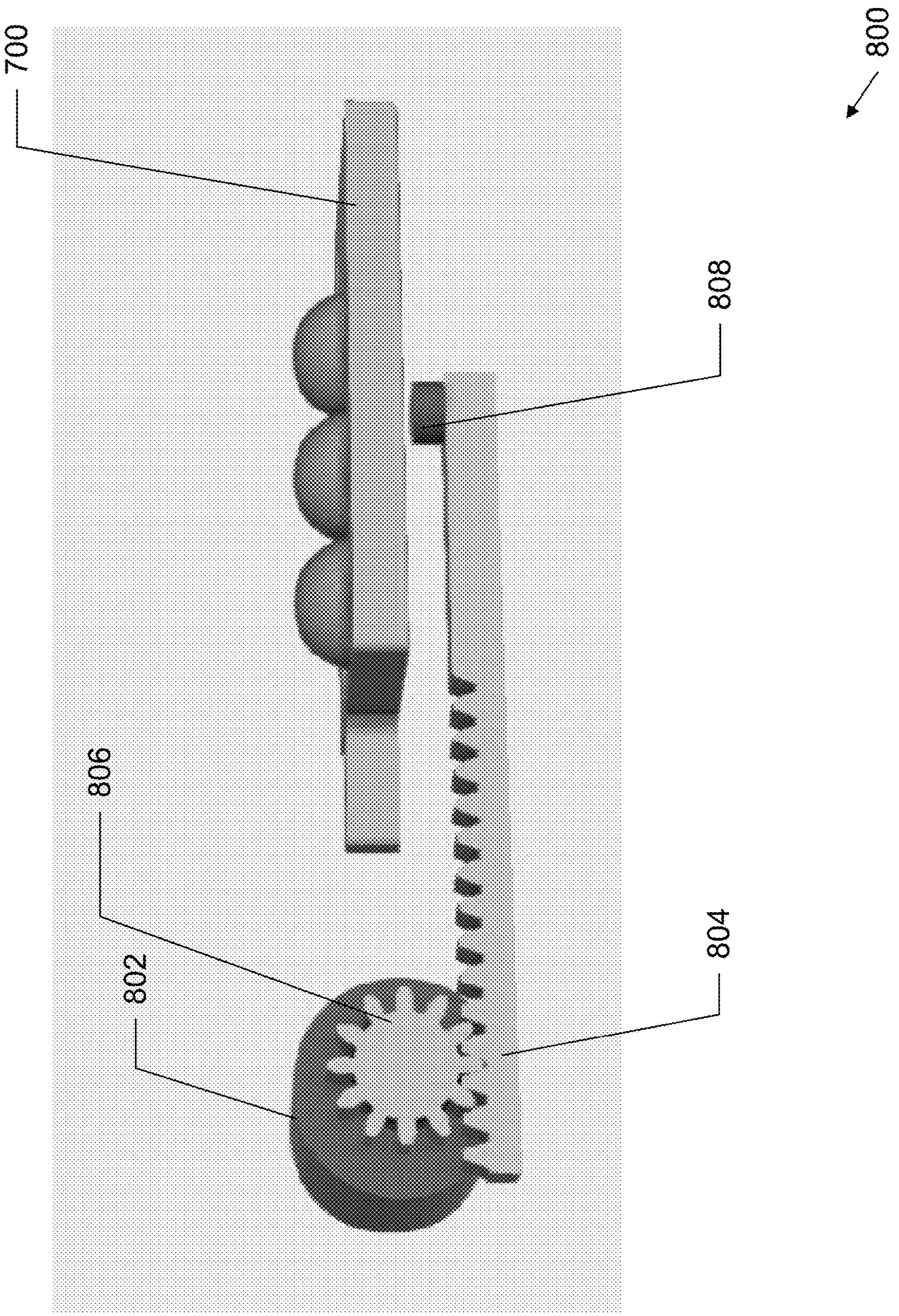
FIG. 8 is an exemplary illustration of a cartridge movement apparatus according to embodiments of the present techniques.

An exemplary cartridge movement apparatus 800, for performing reagent washing and mixing is shown in FIG. 8. In this example, apparatus 800 may include a servo motor 802, a rack 804 and pinion 806 gear mechanism, and a permanent magnet 808. Servo motor 802 may be controlled by control circuitry, as described below, and may turn pinion gear 806, causing movement of rack 804 and thus, movement of permanent magnet 808, which is attached to rack 804. Movement of permanent magnet 808 may be used to move the magnetic particles in cartridge 700. Permanent magnet 808 may, for example, be a neodymium alloy magnet. Using rack and pinion mechanism to move micromagnetic beads inside the cartridge to provide manipulation and movement of micromagnetic beads to achieve mixing and washing actions inside the cartridge reservoirs and for transporting the "washed" micromagnetic beads to the detection reservoir.

Figure 9:
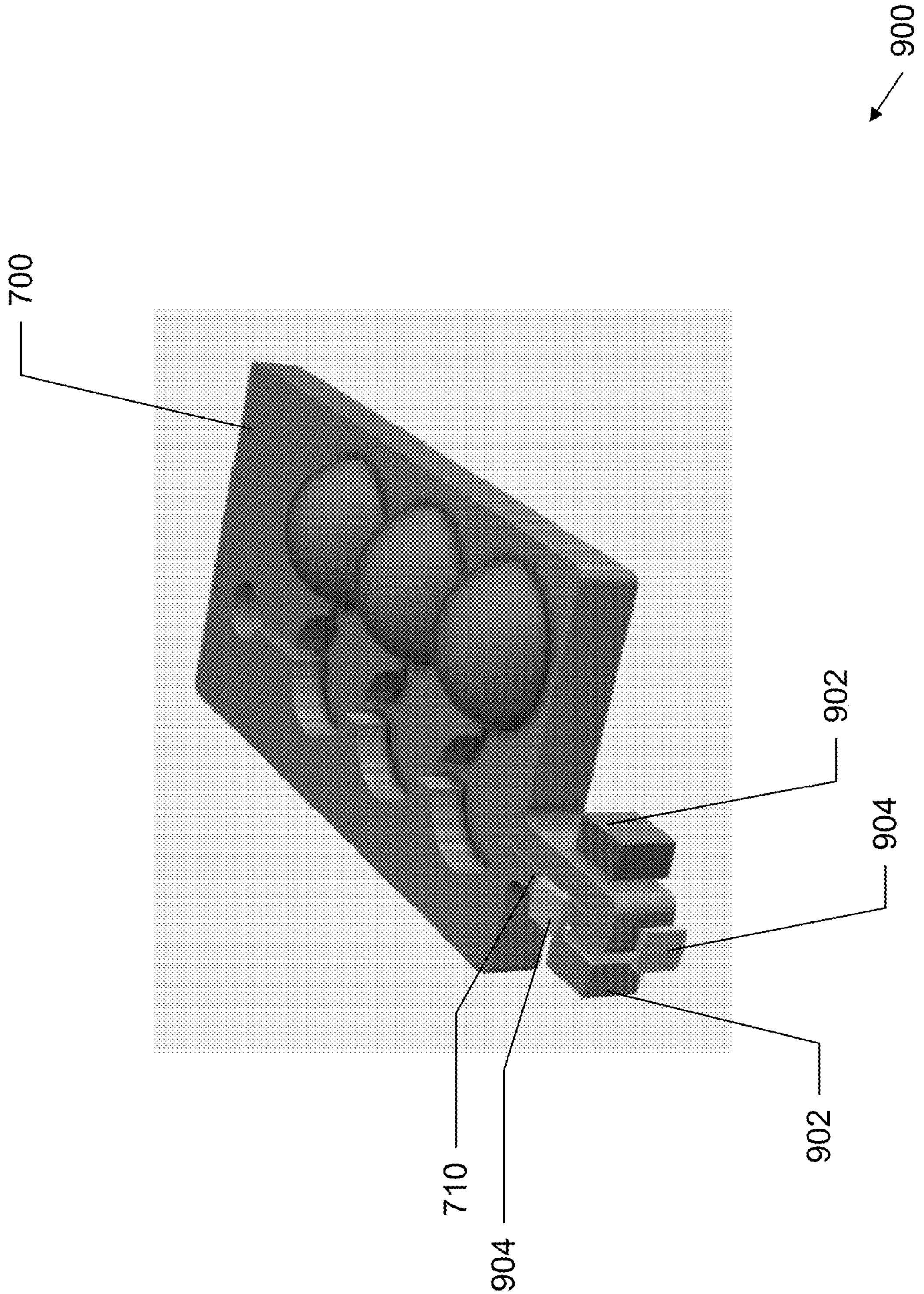
FIG. 9 is an exemplary illustration of an embodiment of fluorescence detection according to embodiments of the present techniques.

An exemplary embodiment of fluorescence detection apparatus 900 is shown in FIG. 9. As shown in this example, Multispectral photodiode chips 902 and excitation LEDs 904 may be arranged adjacent to the detection region in chamber 710, which contains the washed magnetic particles with attached IgA, IgM, and IgG and fluorescent compound. Excitation LEDs 904, as controlled by control circuitry, as described below, may illuminate the contents of chamber 710, causing excitation of fluorescent compounds and emission of light from the fluorescent compounds. Multispectral photodiode chips 902 may receive and detect the emission spectrum of light emitted from the fluorescent compounds, which may be analyzed, for example, by optical sensing circuitry and/or computing devices, as described herein, to determine the presence or absence of COVID-19 infection, antibodies, etc.

Figure 10:
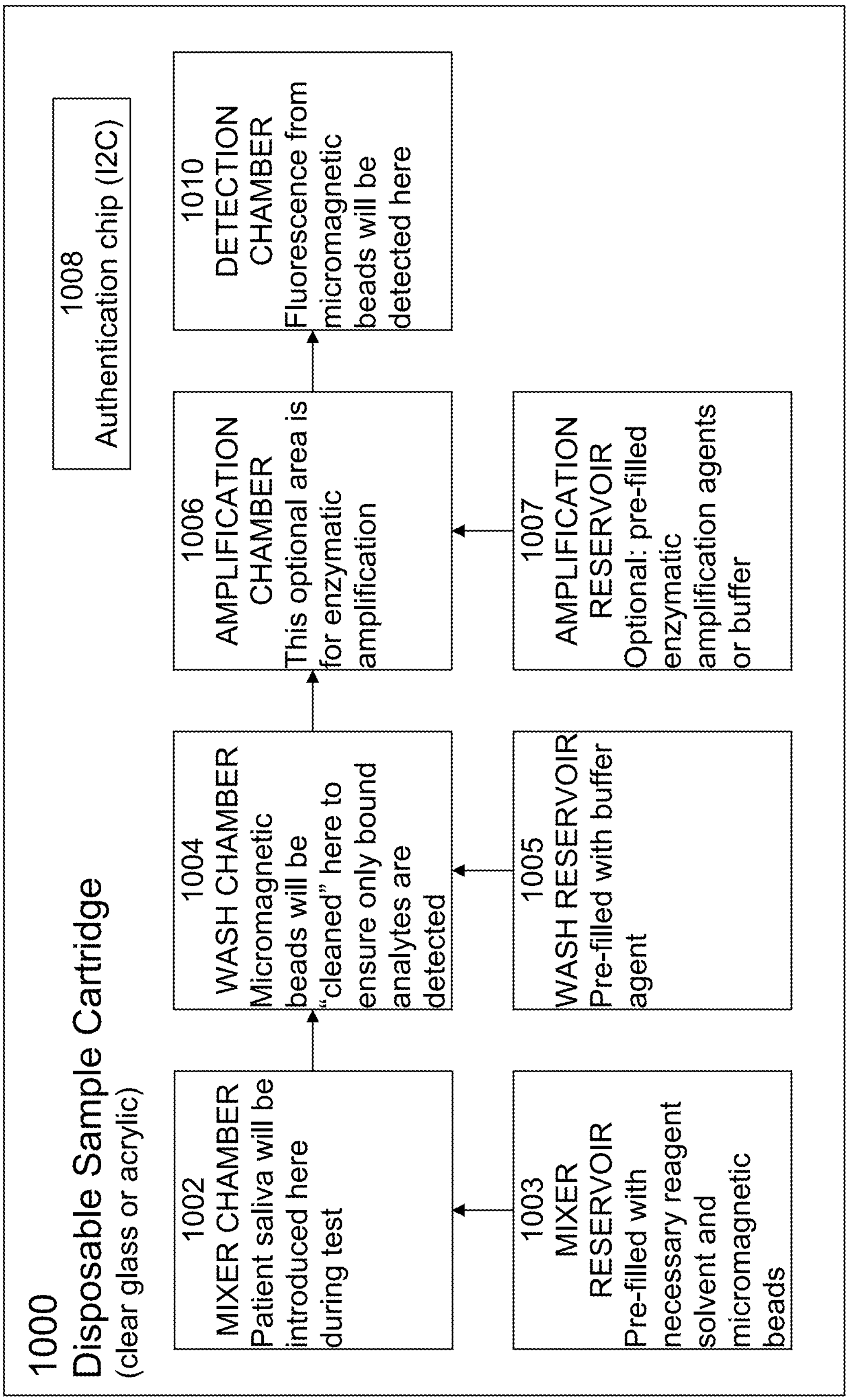
FIG. 10 is an exemplary block diagram of a test cartridge according to embodiments of the present techniques.

An exemplary block diagram of a test cartridge 1000 is shown in FIG. 10. In this example, test cartridge 1000 is a disposable sample cartridge made, for example, from clear glass or silica, transparent acrylic, other plastic, or other transparent material. Cartridge 1000 may include mixer chamber 1002, mixer reservoir 1003, wash chamber 1004, wash reservoir 1005, optional amplification chamber 1006, optional amplification reservoir 1007, detection reservoir 1010, and authentication chip 1008. Reservoirs 1003, 1005, and 1007 may contain solvents, reagents, buffers, etc., in hermetically sealed blisters for storage. Mixer reservoir 1003 may be pre-filled with the necessary reagent solvent and micromagnetic beads or particles having antigens to antibodies raised against SARS-CoV-2 immobilized on the particles. A patient saliva sample may be introduced into mixer chamber 1002 during testing and the reagent solvent and micromagnetic beads may be moved to mixer chamber 1002. Antibodies present in the sample will bind to the antigens immobilized onto magnetic particles. Mixing may be facilitated by movement of the magnetic particles. The magnetic particles may be moved by application of electric current by testing device circuitry to magnetic coils or by movement of cartridge 1000 relative to a magnetic field produced by magnetic coils or by a permanent magnet.

Wash reservoir 1005 may be pre-filled with buffer agent. Micromagnetic beads may be magnetically transported from mixer chamber 1002 to wash chamber 1004, and buffer agent may be moved to wash chamber 1004. In wash chamber 1004, the micromagnetic beads may be "cleaned" to ensure only bound analytes are detected. Optional amplification reservoir 1007 may be prefilled with enzymatic amplification agents or buffer. Micromagnetic beads may be magnetically transported from wash chamber 1004 to amplification chamber 1006, and enzymatic amplification agents or buffer may be moved to amplification chamber 1006. In amplification chamber 1006, optional enzymatic amplification may be performed. Detection reservoir 1010 may be pre-filled with buffer agent. Micromagnetic beads may be magnetically transported from wash reservoir 1004 or optional amplification chamber 1006 to detection reservoir 1010, where, for infected patients, fluorescence from micromagnetic beads may be detected by way of illuminating LEDs and multi-spectrum photodiodes, as described herein.

Figure 11:
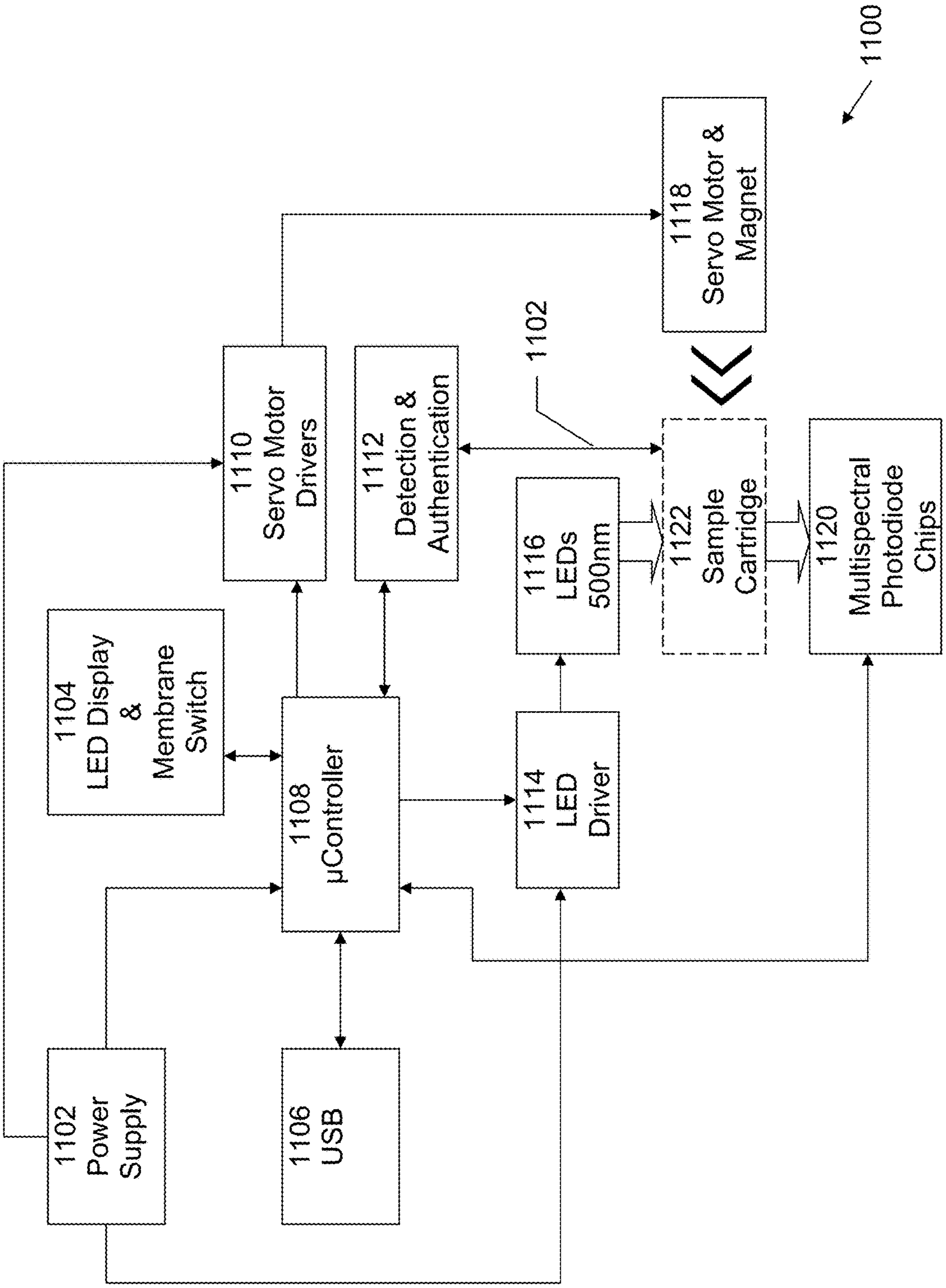
FIG. 11 is an exemplary block diagram of a testing device according to embodiments of the present techniques.

An exemplary block diagram of a testing device 1100 is shown in FIG. 11. In this example, testing device 1100 may include power supply 1102, user interface 1104, such as an LED display and membrane switch buttons, communication interface 1106, such as a USB port or wireless communications adapter, microcontroller 1108, servo motor drivers 1110, detection and authentication circuitry 1112, LED driver 1114, sample excitation LEDs 1116, servo motor, rack and pinion, and magnet assembly 1118, light detector 1120, and insertable sample cartridge(s) 1122. Power supply 1102 may provide electrical power to the other components of testing device 1100 and may include batteries or other electrical and electronic components, such as voltage regulators to provide different voltage supply levels as needed. User interface 1104, may include, for example, an LED display and membrane switch buttons, or other display and/or input/output devices. Embodiments may include other configurations of front panel, as well as other display devices, such as LCD displays, numeric displays, etc., which may display additional information, such as concentration, amount, percentage, etc., of antibodies, fluorescent indicator, threshold levels, etc.

Communication interface 1106, may include, for example a USB port or wireless communications adapter, such as Wi-Fi, Bluetooth, cellular data, or other wireless communications technique. Microcontroller 1108 may include one or more processors, memory, input/output circuitry, and other circuitry to control the operation of testing device 1100 and to provide interfacing to external computers for data transfer of information including test results, patient information, etc., via USB port or wireless communications adapter and to provide interfacing to the authentication chip on the sample cartridge. Servo motor drivers 1110 may include electronic circuitry to provide electrical current to drive the operation of servo motor 1118 as controlled by microcontroller 1108. Detection and authentication circuitry 1112 may include circuitry to interface microcontroller 1108 with authentication chip 718, 1008, shown in FIGS. 7 and 10. Such authentication chips may include authentication circuitry, identification circuitry, data storage circuitry, etc., and may identify the type of chip, the type of testing being performed, the patient being tested, etc. Detection and authentication circuitry 1112 may allow microcontroller 1108 to access this information, allowing configuration of testing device 1100 based thereupon, for example, allowing the device to work in "live" or "testing" mode as required.

LED driver 1114 may include electronic circuitry to provide electrical current to drive the operation of sample excitation LEDs 1116, as controlled by microcontroller 1108. Sample excitation LEDs 1116 may provide light to excite the fluorescent compounds in the sample under test, as described herein. For example, sample excitation LEDs may emit light for excitation of fluorescent compounds at 500 nm wavelength, or other suitable wavelength for excitation of the fluorescent compounds. Multiple LEDs may be provided to increase the intensity, as well as to achieve a more uniform illumination of the sample. Servo motor, rack and pinion, and magnet assembly 1118 may include, for example, the apparatus shown in FIG. 8, and described in reference thereto. Light detector 1120 may include electronic circuitry to detect light emitted by the excited fluorescent compounds in the sample under test, as described herein. Light detector 1120 may, for example, include multispectral photodiodes chips, such as the AMS® multichannel AS7265x chipset, or other suitable light detectors. Sample cartridge 1120 may include, for example, a test cartridge 700 similar to that shown in FIGS. 7*a*, 7*b*, 9, 10, etc.

Figure 12B:
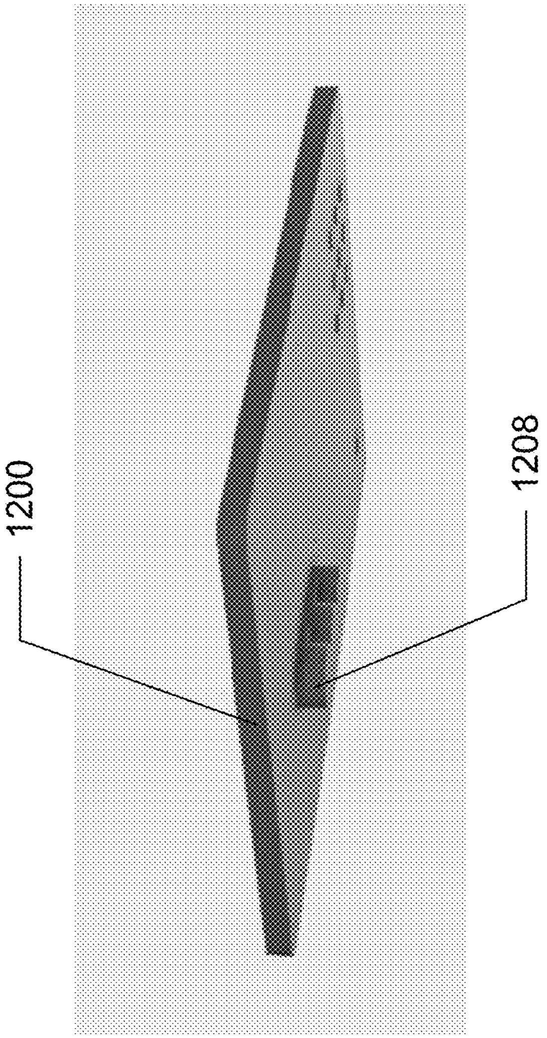
FIG. 12*b* is an exemplary illustration of a front panel of a testing device according to embodiments of the present techniques.
Figure 12A:
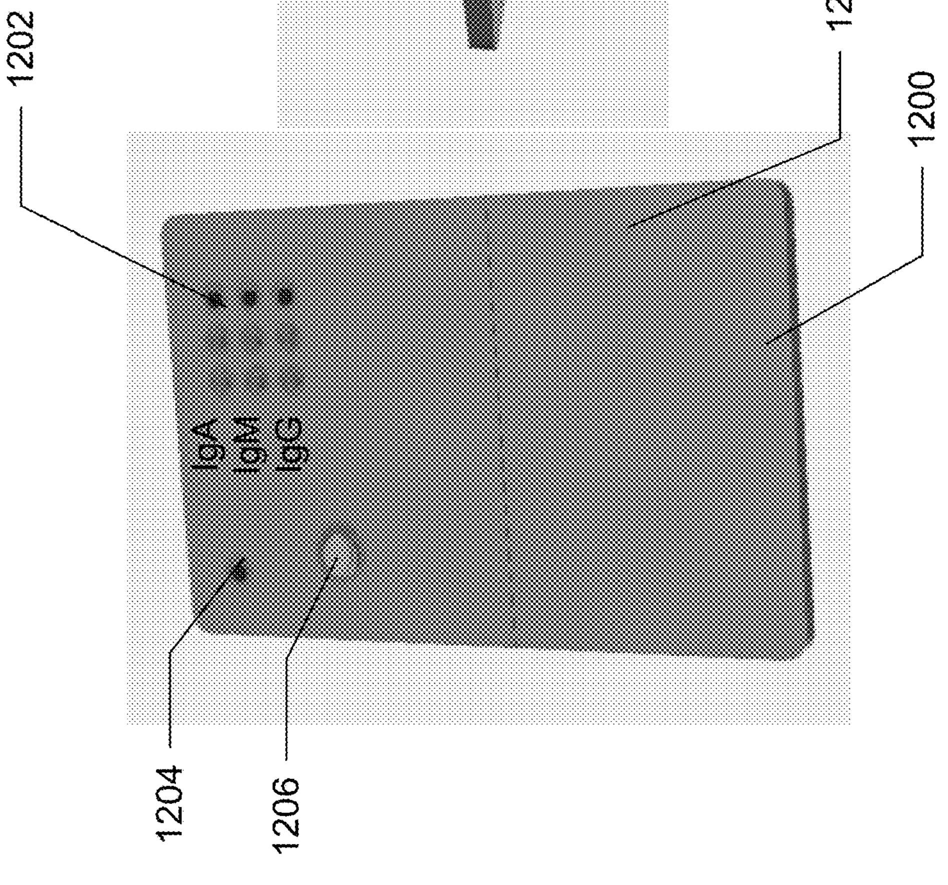
FIG. 12*a* is an exemplary illustration of a front panel of a testing device according to embodiments of the present techniques.
Figures 3, 16:
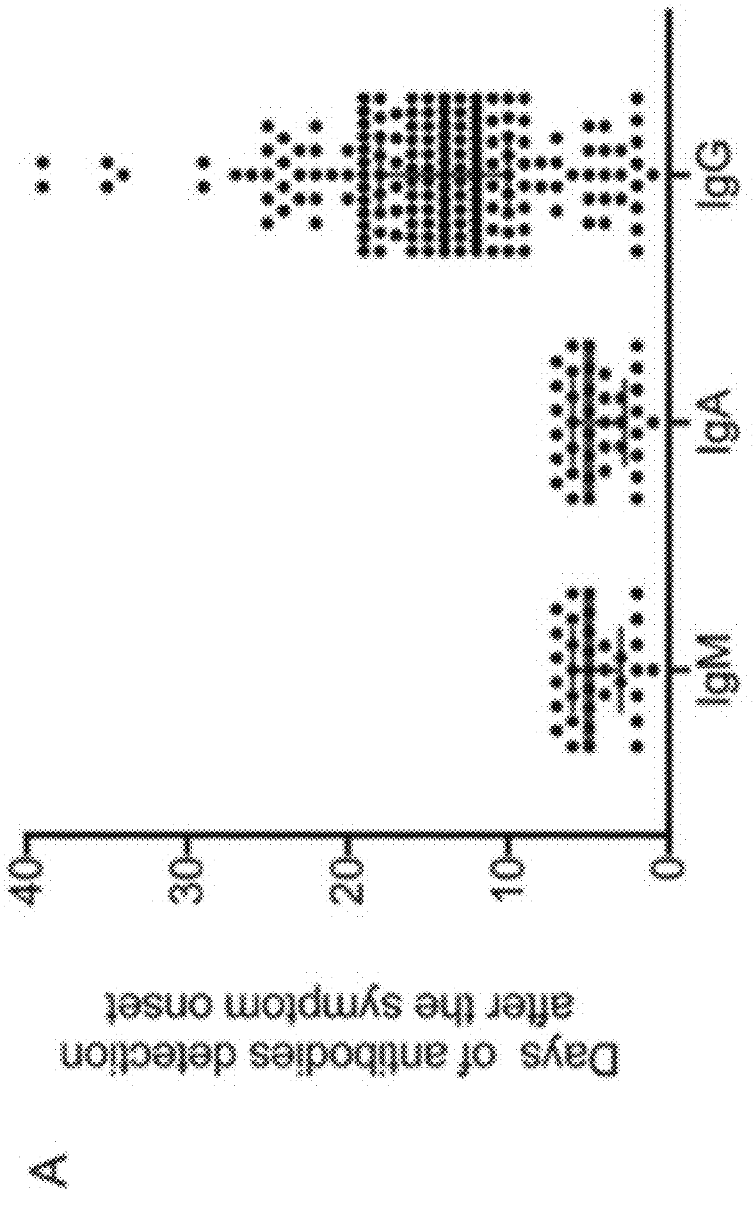
FIG. 16 is an exemplary block illustration of antibody types present at different stages of disease, as may be utilized by embodiments of the present techniques.

An exemplary front view of a front panel 1200 of testing device 1100 is shown in FIG. 12*a*. In this example, front panel 1200 may include test result indicators 1202, test in progress indicator 1204, and operation switch 1206. In this example, test result indicators 1202 may include three by three LEDs (red, yellow, green) to provide intuitive test result based on predetermined threshold levels for IgA, IgM, and IgG. In embodiments, only one color (green, yellow, or red) will result for each antibody. For example, a green light may indicate the user sample is positive for the respective antibody, a red light may indicate the user does not have the respective antibody in high enough quantities to be detected by the device, a yellow light may indicate an indeterminate result. Research may show (for example, see FIG. 16 and Table 1) that IgA and IgM are produced and persist in early stages of the disease (Days 0-14), and IgG is produced starting on Day 0 of the disease and levels plateau after Day 20 (Guo, et al., 2020).

TABLE 1

| | |
|---|---|
| IgA | early stage |
| IgM | early stage |
| IgA + IgM | early stage |
| IgA + IgG | early stage |
| IgM + IgG | early stage |
| IgA + IgM + IgG | early stage |
| IgG | late stage |

This may roughly imply that a positive for IgA or IgM means the patient is in early stages of infection, and the presence of IgG alone means the patient is in later stages of infection. Thus, embodiments may detect which of the patients has a mounted immune response to the virus. As the test will be able to detect which antibodies bind to the spike protein, which is the protein that binds to the ACE receptors in the lungs to cause infection, this test may be able to detect which patients have raise neutralizing antibodies toward the virus.

Returning to FIG. 12*a*, test in progress indicator 1204 may include a status LED indicating the test in progress. Operation switch 1206 may include a membrane switch for an operator to start the test process. Embodiments may include other configurations of front panel, as well as other display devices, such as LCD displays, numeric displays, etc., which may display additional information, such as concentration, amount, percentage, etc., of antibodies, fluorescent indicator, threshold levels, etc.

An exemplary rear view of a front panel 1200 of testing device 1100 is shown in FIG. 12*b*. In this example, front panel 1200 may include a plurality of spring-backed actuators 1208 in a closable door portion 1210 of front panel 1200 to apply pressure, when the door is closed, to the reservoir blisters and move the reagents, solvents, and buffers, etc. into their associated chambers.

Figure 13B:
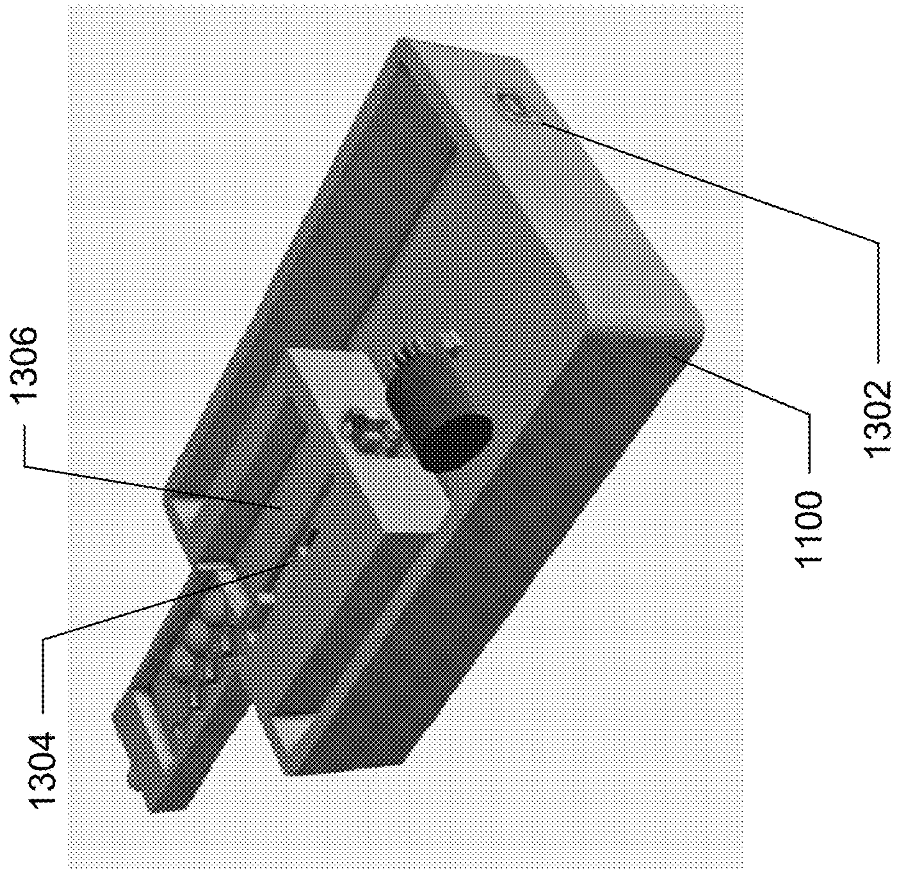
FIG. 13*b* is an exemplary internal view of a testing device according to embodiments of the present techniques.
Figure 13A:
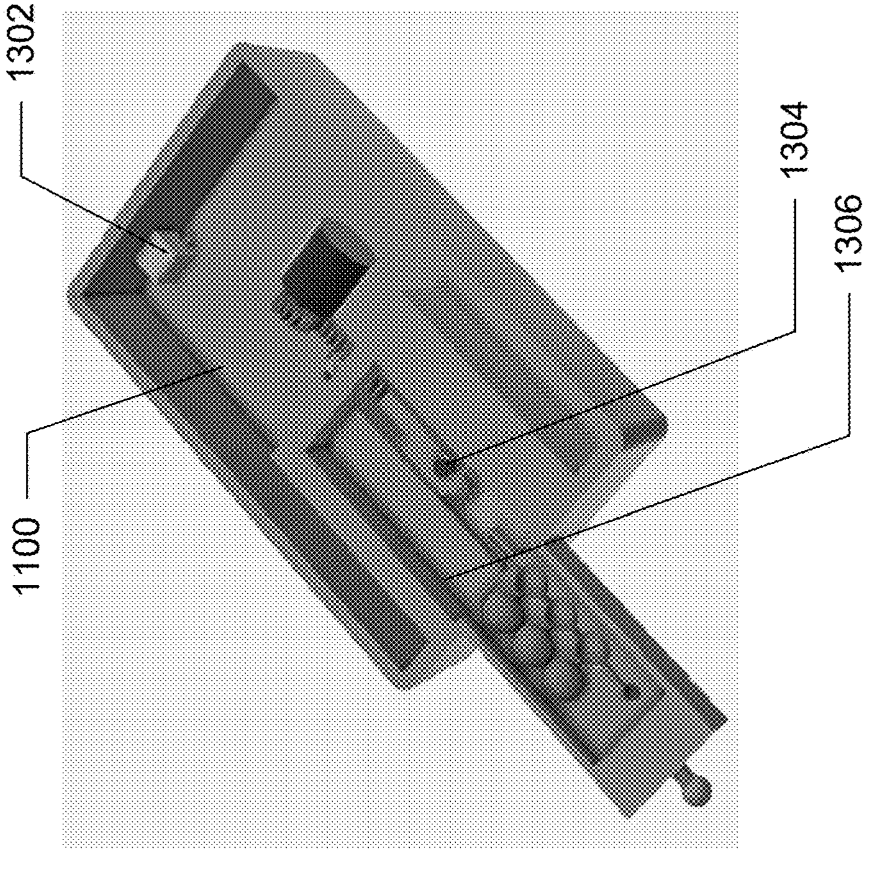
FIG. 13*a* is an exemplary internal view of a testing device according to embodiments of the present techniques.

An exemplary internal view of testing device 1100 is shown in FIGS. 13*a* and 13*b*. In this example, USB-B connector 1302, authentication chip reader connector 1304, and cartridge holder tray 1306 are shown.

Figure 17:
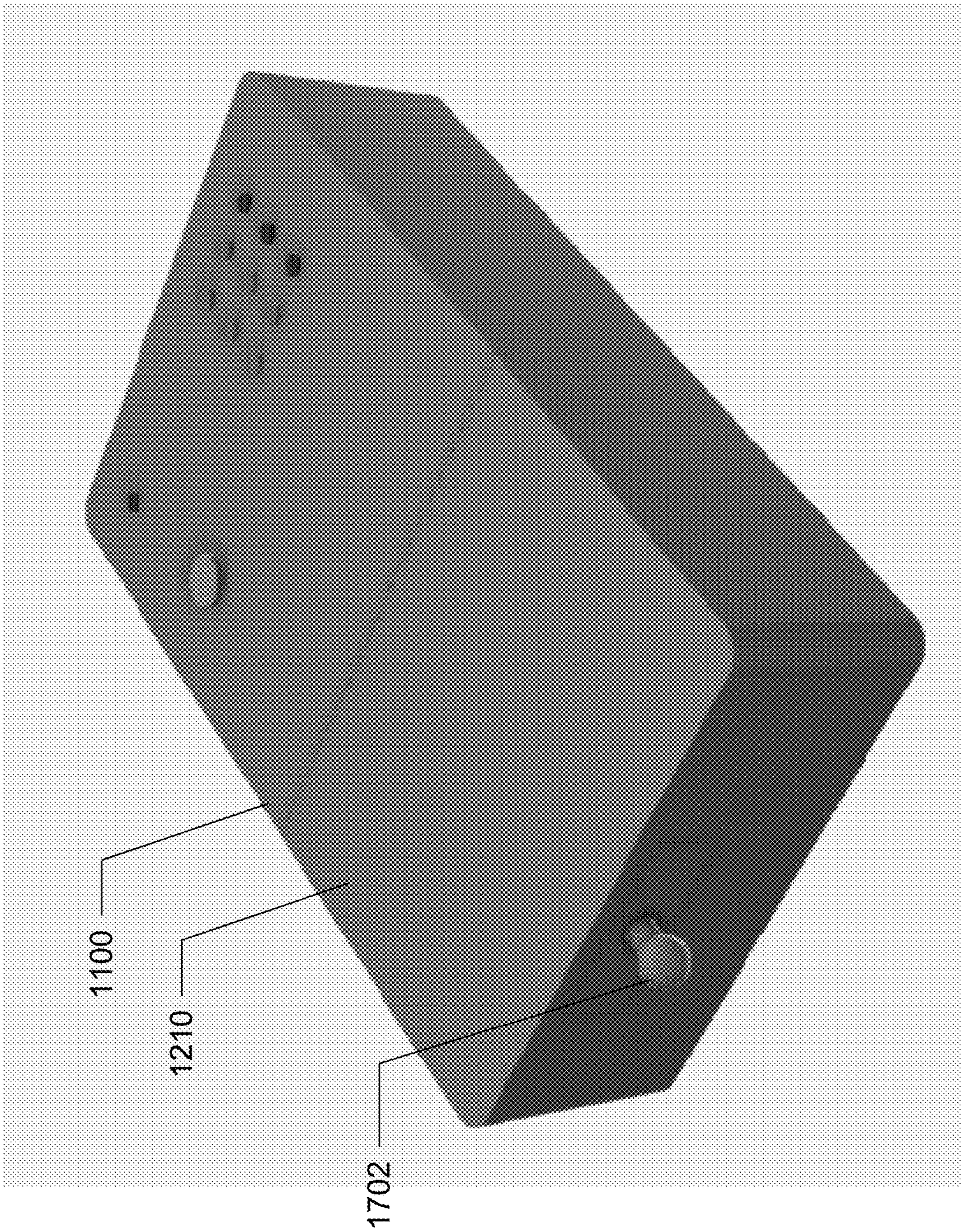
FIG. 17 is an exemplary internal view of a testing device according to embodiments of the present techniques.

An exemplary external view of testing device 1100 is shown in FIG. 17. In this example, after a sample cartridge is inserted into testing device 1100, door 1210 may be closed and a latch 1702 may be activated, preventing removal of the cartridge during the test. When door 1210 is closed, spring-backed actuators 1208, shown in FIG. 12*b*, may apply pressure to the reservoir blisters and move the reagents, solvents, and buffers, etc. into their associated chambers.

Figure 14:
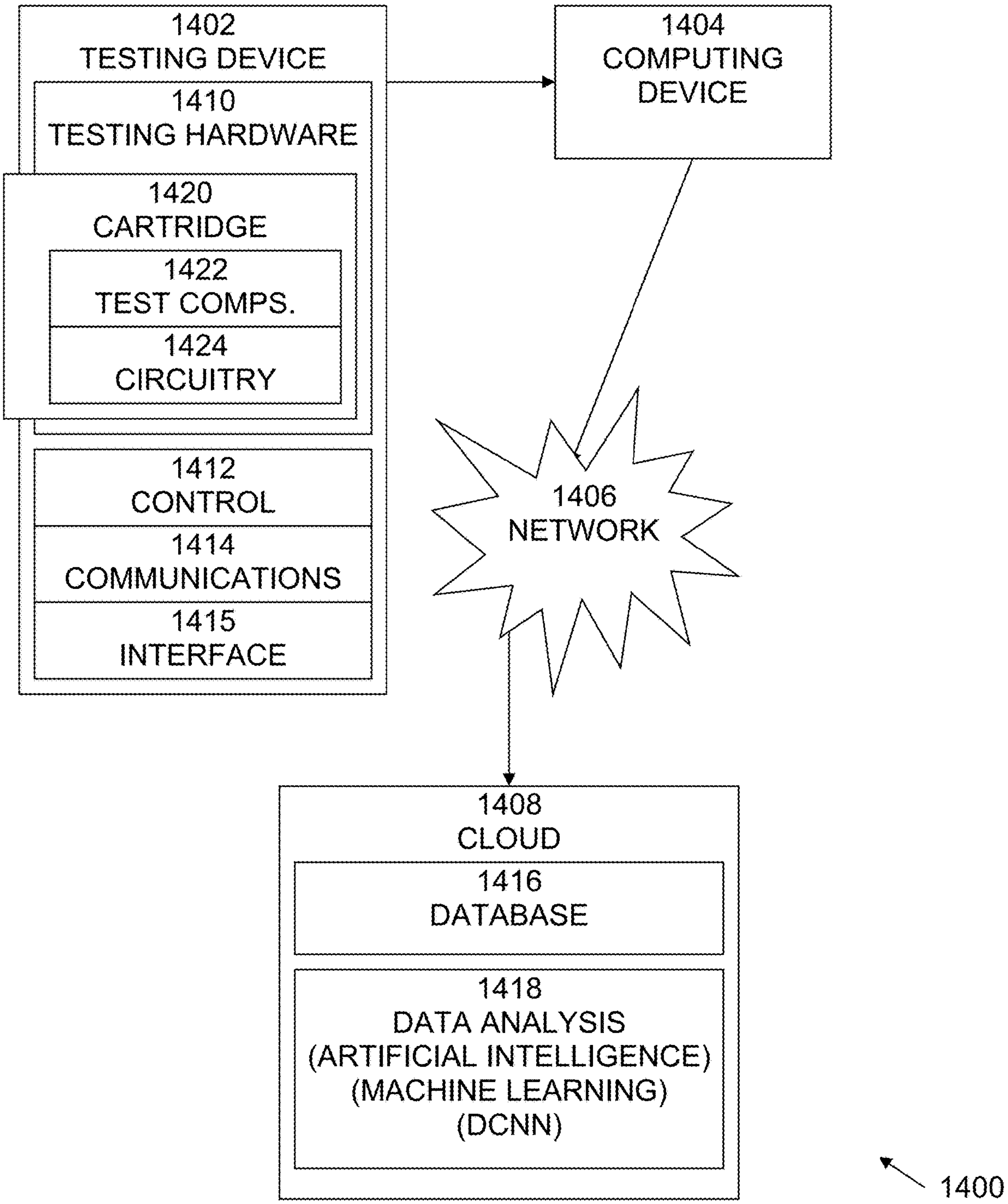
FIG. 14 is an exemplary block diagram of a testing system according to embodiments of the present techniques.

An exemplary testing system 1400 is shown in FIG. 14. System 1400 may include testing device 1402, computing device 1404, network 1406, and cloud computing system 1408. Testing device 1402 may be a stand-alone or integrated device and may include testing hardware 1410, control circuitry 1412, and communications circuitry 1414. Testing hardware 1410 may include the components shown in FIGS. 3, 4, and/or 5, as described above, and that performs the testing functions described above. Testing hardware 1410 may include components to interface with an inserted test cartridge 1420, which may include test components 1422, such as a microfluidic silica chip with etched capillaries and chambers, and circuitry 1424, which may include authentication circuitry, identification circuitry, data storage circuitry, etc. Testing hardware 1410 may further include components such as circuitry to apply, and to control the application of, electric current to magnetic coils that may be formed on cartridge 1420 or that may be present in the testing device 1402 and may be adjacent to or in the vicinity of cartridge 1420. Control circuitry 1412 may include control logic, controller, or processor circuitry to control performance of the physical, optical, electrical, and computing processes involved in operating testing device 1402, such as controlling the electric current in the magnetic coils, and in performing the functions described above. Communications circuitry 1414 may include circuitry to provide wired and/or wireless communications with one or more external or integrated devices, such as computing device 1404. In embodiments, testing device 1402 may also include interface 1415, which may include indicator or display components for direct display of test results from testing device 1402 and/or buttons, etc., for direct entry of information into testing device 1402.

Computing device 1404 may be an integrated or standalone device, such as a smartphone, tablet computer, laptop computer, personal computer, workstation computer, cloud computing service, etc., to communicate with testing device 1402. Computing device 1404 may provide processing and analysis of data received from testing device 1402, as well as communications with testing device 1402 and with cloud computing system 1408 vis network 1406. In embodiments, computing device 1404 may also include indicator or interface displays (not shown) for display of test results from testing device 1402 and/or entry of information into testing device 1402. Network 1406 may be any public or proprietary LAN or WAN, including, but not limited to the Internet, carrier network, wireless network, etc. Cloud computing system 1408 may provide on-demand availability of computer system resources, such as database storage 1416 and computing power/data analysis 1418, which is typically implemented in data centers available to many users over the Internet.

In embodiments, the optical analysis may result in imaging representative of sample 402. The resulting imaging, using machine learning techniques, may be used to detect protein structure geometry (Daaboul, G. G., et al. 2017). Then, combined inputs from chemical lab-on-chip sensors and the optical sensors, both included in testing hardware 1410 may be analyzed 1418, for example, using cloud computing system 1408, using both commonly available and proprietary Artificial Intelligence/Machine Learning (AI/ML) architectures, such as a Deep Cognitive Neural Network (DCNN), such as that described in U.S. Patent Application Publication No. 2019/0156189, published May 23, 2019, which is hereby incorporated by reference herein. Machine learning algorithms may be trained to detect the coronavirus family of viruses, and over time, using additional sample data, will become more effective at identifying different strains of the virus.

In embodiments, the machine algorithms may be further trained to detect other classes of viruses and specific strains of viruses or other pathogens, or trained for detection of neurodegenerative disease markers. The computing device 1404 computational platform may interface with a cloud computing platform 1408, opening up applications using anonymized patient and third party data.

Figure 15:
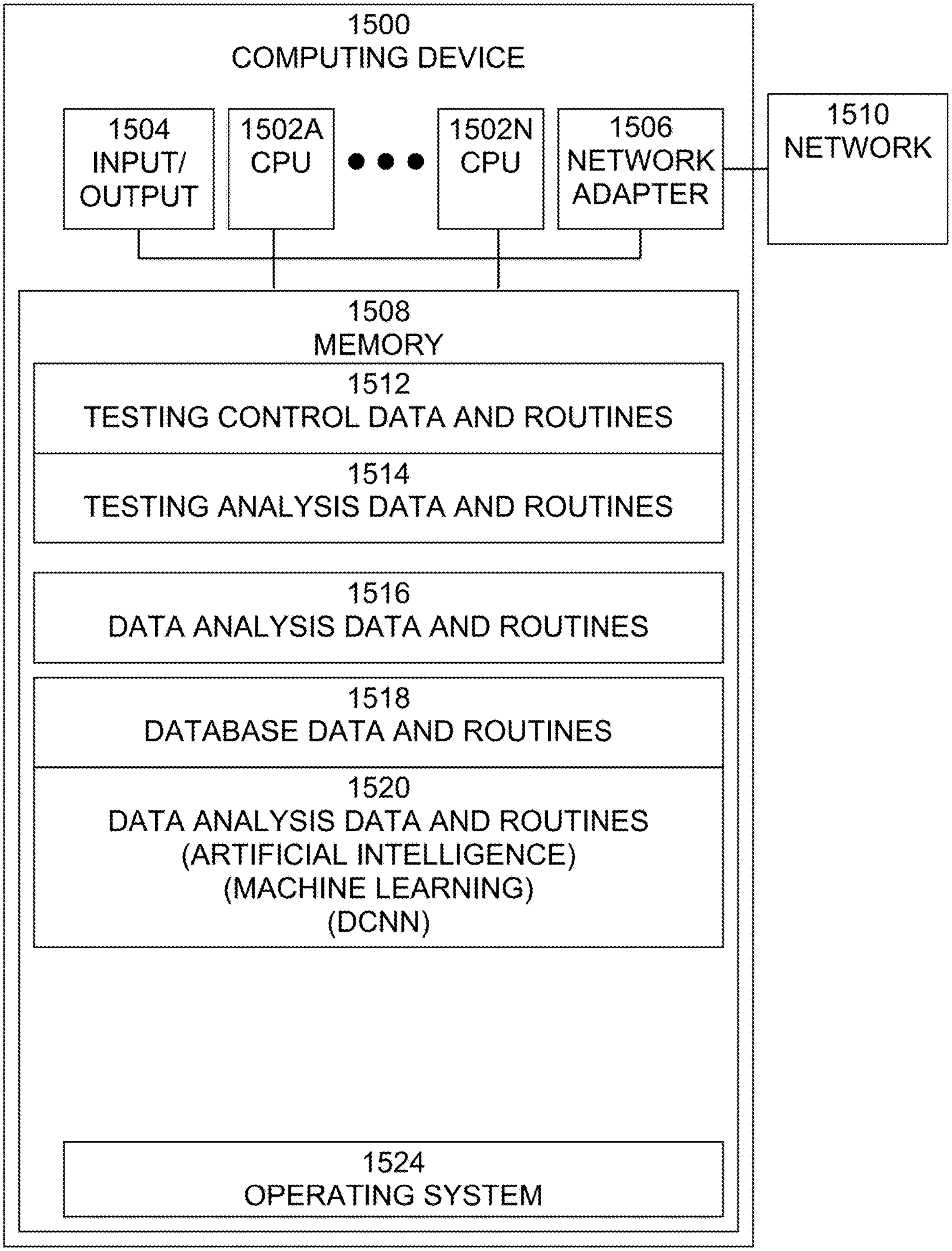
FIG. 15 is an exemplary block diagram of a computing device, in which processes involved in the embodiments described herein may be implemented.

An exemplary block diagram of a computing device 1500, in which processes involved in the embodiments described herein, such as computing device 1406 or cloud computing system 1408, may be implemented, is shown in FIG. 15. Computing device 1500 may be implemented using one or more programmed general-purpose computer systems, such as embedded processors, systems on a chip, personal computers, workstations, server systems, and minicomputers or mainframe computers, or in distributed, networked computing environments. Computing device 1500 may include one or more processors (CPUs) 1502A-1502N, input/output circuitry 1504, network adapter 1506, and memory 1508. CPUs 1502A-1502N execute program instructions in order to carry out the functions of the present communications systems and methods. Typically, CPUs 1502A-1502N are one or more microprocessors, such as an INTEL CORE® processor. FIG. 15 illustrates an embodiment in which computing device 1500 is implemented as a single multi-processor computer system, in which multiple processors 1502A-1502N share system resources, such as memory 1508, input/output circuitry 1504, and network adapter 1506. However, the present communications systems and methods also include embodiments in which computing device 1500 is implemented as a plurality of networked computer systems, which may be single-processor computer systems, multi-processor computer systems, or a mix thereof.

Input/output circuitry 1504 provides the capability to input data to, or output data from, computing device 1500. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 1506 interfaces device 1500 with a network 1510. Network 1510 may be any public or proprietary LAN or WAN, including, but not limited to the Internet.

Memory 1508 stores program instructions that are executed by, and data that are used and processed by, CPU 1502 to perform the functions of computing device 1500. Memory 1508 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 1508 may vary depending upon the function that computing device 1500 is programmed to perform. In the example shown in FIG. 15, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present systems and methods may include any and all such arrangements.

In the example shown in FIG. 15, memory 1508 may include, in the case of a testing device 1402, testing control data and routines 1512, testing analysis data and routines 1514, in the case of a computing device 1404, data analysis data and routines 1518, and in the case of a cloud computing system 1408, database data and routines 1520, and data analysis data and routines 1522 and operating system 1524.

Testing control data and routines 1512 may include software routines to control performance of the physical, optical, electrical, and computing processes involved in operating testing device 1402, as well as data obtained from such testing, as described above. Testing analysis data and routines 1514 may include software routines to perform initial analysis and derivation of data obtained from testing, as described above. Data analysis data and routines 1514 may include, which may include software routines to perform processing and analysis of data received from testing device 1402, as described above. Authentication/matching routines 1514 may include modular proximity test routines 1518, which may include software routines to perform modular proximity testing on received authentication data, as described above. Database data and routines 1520, may include software routines to provide database storage of data on cloud computing system 1408, as described above. Data analysis data and routines 1522 may include software routines to provide computing power/data analysis on cloud computing system 1408, as described above. Operating system 1524 may provide overall system functionality.

As shown in FIG. 15, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A device for detecting primary antibodies to a pathogen or the pathogen comprising:

a mechanism configured to hold a cartridge configured to receive a test sample, the cartridge comprising:

a first chamber configured to receive the test sample, the first chamber hermetically sealed and pre-filled with micromagnetic particles having antigens adapted to bind to antibodies raised against the pathogen immobilized on the micromagnetic particles, a first reservoir hermetically sealed and pre-filled with secondary antibodies labeled with a fluorescent compound, the secondary antibodies adapted to bind to antigens that have bound to antibodies raised against the pathogen, a detection region, and an authentication chip operable to identify a type of test being performed and/or a patient being tested, wherein the authentication chip is operable to interface with a microcontroller external to the cartridge;

a mechanism configured to move a magnetic device relative to the cartridge;

a mechanism configured to move the secondary antibodies from the first reservoir to the first chamber;

a computer system comprising a processor, memory to store program instructions and data and accessible by the processor, and program instructions stored in the memory and executable by the processor to control the mechanism configured to move the magnetic device to:

mix the micromagnetic particles with the test sample by moving the micromagnetic particles, so as to facilitate binding of the antigens immobilized on the micromagnetic particles to the antibodies raised against the pathogen, mix the micromagnetic particles with the secondary antibodies from the first reservoir in the first chamber, so as to facilitate binding of the secondary antibodies labeled with the fluorescent compound to the antigens that have bound to antibodies raised against the pathogen, and move the micromagnetic particles to the detection region after the secondary antibodies labeled with the fluorescent compound have bound to the antigens that have bound to antibodies raised against the pathogen; and circuitry configured to detect fluorescence of the fluorescent compound in the detection region, the circuitry comprising:

a light source configured to emit a plurality of wavelengths of light arranged to illuminate the detection region so as to excite emitted fluorescence from the fluorescent compound and to cause wavelength backscattering with the plurality of wavelengths of light, and an optical sensor and circuitry configured both to analyze parameters of a spectrum of the emitted fluorescence from the fluorescent compound in the detection region and to analyze the backscattered light, to perform wavelength and amplitude analysis on both the emitted light and the backscattered light, and determine the absence, presence and quantity and isotype of antibodies in the test sample, and to output a signal representing the determined absence, presence, and quantity and isotype of antibodies in the test sample;

wherein the parameters of the spectrum comprise a wavelength distribution of the emitted fluorescence.

2. The device of claim 1, wherein the mechanism configured to move the magnetic device comprises a servo motor controlled by the processor and rack and pinion gearing to move the magnetic device.

3. The device of claim 2, wherein the magnetic device comprises a permanent magnet or a magnetic coil.

4. The device of claim 3, wherein the light source comprises:

at least one of a plurality of light emitting diodes, laser diodes, other lasers, or a tunable laser.

5. The device of claim 4, wherein the processor is configured to receive the signal representing the detected fluorescence and the program instructions stored in the memory further include program instructions configured to determine presence of primary antibodies to the pathogen or the pathogen based on the received signal.

6. The device of claim 5, further comprising a display configured to display presence of primary antibodies to the pathogen or the pathogen, wherein the display is connected to the processor, and the program instructions stored in the memory further include program instructions configured to control the display based on the determined presence of primary antibodies to the pathogen or the pathogen.

7. The device of claim 1, wherein the cartridge further comprises:

a second chamber between the first chamber and the detection region and configured to receive contents of the first chamber, and a second reservoir filled before use of the cartridge in the device for detecting primary antibodies with buffer agent.

8. The device of claim 7, further comprising a mechanism configured to move the buffer agent from the second reservoir to the second chamber.

9. The device of claim 8, wherein the program instructions stored in the memory further include program instructions configured to control the mechanism configured to move the magnetic device to move the micromagnetic particles from the first chamber to the second chamber after the secondary antibodies labeled with the fluorescent compound have bound to the antigens that have bound to the antibodies raised against the pathogen.

* * * * *